US012648728B2

(12) United States Patent
Smith et al.

(10) Patent No.: US 12,648,728 B2
(45) Date of Patent: Jun. 9, 2026

(54) FOLD DETECTION OF AN IMPLANTABLE ELECTRODE ARRAY

(71) Applicant: Cochlear Limited, Macquarie University (AU)

(72) Inventors: Zachary Mark Smith, Macquarie University (AU); Matthew Zygorodimos, Macquarie University (AU); Ryan Orin Melman, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 498 days.

(21) Appl. No.: 18/022,472

(22) PCT Filed: Sep. 7, 2021

(86) PCT No.: PCT/IB2021/058138

§ 371 (c)(1),
(2) Date: Feb. 21, 2023

(87) PCT Pub. No.: WO2022/058840

PCT Pub. Date: Mar. 24, 2022

(65) Prior Publication Data

US 2023/0309891 A1     Oct. 5, 2023

Related U.S. Application Data

(60) Provisional application No. 63/078,711, filed on Sep. 15, 2020.

(51) Int. Cl.
    *A61B 5/279*     (2021.01)
    *A61B 5/00*     (2006.01)
    (Continued)

(52) U.S. Cl.
    CPC ............ *A61B 5/279* (2021.01); *A61B 5/6817* (2013.01); *A61N 1/36038* (2017.08); *A61N 1/0541* (2013.01)

(58) Field of Classification Search
    CPC .............. A61N 1/0541; A61N 1/36038; A61N 1/36039
    See application file for complete search history.

(56) References Cited

U.S. PATENT DOCUMENTS 6,636,768 B1     10/2003     Harrison
9,186,081 B2     11/2015     Afonso et al.
                (Continued)

FOREIGN PATENT DOCUMENTS

WO     WO 2019/162837 A1     8/2019

OTHER PUBLICATIONS

F. J. Vanpoucke, P. -P.B. Boermans and J. H. Frijns, "Assessing the Placement of a Cochlear Electrode Array by Multidimensional Scaling," in IEEE Transactions on Biomedical Engineering, vol. 59, No. 2, pp. 307-310, Feb. 2012, doi: 10.1109/TBME.2011.2173198.*
                (Continued)

*Primary Examiner* — Allen Porter
(74) *Attorney, Agent, or Firm* — Knobbe, Martens, Olson & Bear, LLP

(57) ABSTRACT

A method includes receiving a measurement set comprising a plurality of measurement values generated using a plurality of electrodes distributed along an elongate structure configured to be implanted in and/or on a body portion of a recipient. The measurement set is indicative of a pose of the elongate structure relative to the body portion. The method further includes generating, in response at least in part to the measurement set, a gradient vector dataset comprising a plurality of gradient vector phase values. The method further includes generating, in response at least in part to the
                (Continued)

gradient vector dataset, an evaluation of the pose of the elongate structure relative to the body portion.

33 Claims, 12 Drawing Sheets

(51) Int. Cl.
    *A61N 1/05*        (2006.01)
    *A61N 1/36*        (2006.01)

(56) References Cited

U.S. PATENT DOCUMENTS

| | | | |
|---|---|---|---|
| 9,987,490 | B2 | 6/2018 | Kabot et al. |
| 12,172,002 | B2 * | 12/2024 | Zygorodimos ...... A61B 5/6817 |
| 2012/0316454 | A1 * | 12/2012 | Carter .................. A61N 1/0541 |
| | | | 607/57 |
| 2014/0343388 | A1 | 11/2014 | Thakur et al. |
| 2015/0088225 | A1 | 3/2015 | Noble et al. |
| 2015/0112408 | A1 | 4/2015 | Kals |
| 2015/0314122 | A1 | 11/2015 | Kabot |
| 2016/0059015 | A1 | 3/2016 | Risi et al. |
| 2018/0140829 | A1 | 5/2018 | Rams de Miguel, Sr. et al. |
| 2018/0280687 | A1 * | 10/2018 | Carter ...................... A61N 1/08 |
| 2020/0129764 | A1 | 4/2020 | Johnston et al. |
| 2020/0376269 | A1 * | 12/2020 | Carter ................ A61N 1/36039 |
| 2021/0228878 | A1 * | 7/2021 | Koka ................... A61B 5/6886 |

OTHER PUBLICATIONS

C. K. Giardina, E. S. Krause, K. Koka and D. C. Fitzpatrick, "Impedance Measures During in vitro Cochlear Implantation Predict Array Positioning," in IEEE Transactions on Biomedical Engineering, vol. 65, No. 2, pp. 327-335, Feb. 2018, doi: 10.1109/TBME.2017.2764881.*

Extended European Search Report in Application No. 21868822.4, dated Sep. 3, 2024 in 8 pages.

International Search Report for PCT Application No. PCT/IB2021/058138 dated Dec. 9, 2021 in 5 pages.

Written Opinion for PCT Application No. PCT/IB2021/058138 dated Dec. 9, 2021 in 6 pages.

Van Der Graaf, J., "Monitoring Electrode Array Tip Fold-over in Cochlear Implantation," MSc Thesis—Biomedical Engineering, Delft University of Technology, pp. 1-71, May 21, 2019.

* cited by examiner

FIG. 5A:

FOLD DETECTION OF AN IMPLANTABLE ELECTRODE ARRAY

BACKGROUND

Field

The present application relates generally to systems and methods for monitoring the implantation of medical devices within the body of a recipient, and more specifically, to facilitating positioning of stimulation elements of a cochlear-implanted auditory prosthesis.

Description of the Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect disclosed herein, a system comprises at least one data input interface configured to receive data from a plurality of transducers of a medical device on or in a recipient. The system further comprises at least one controller in operative communication with the at least one data input interface. The at least one controller is configured to receive a plurality of measurement values generated using the plurality of transducers of the medical device in and/or on a body portion of a recipient. The at least one controller is further configured to utilize the plurality of measurement values to generate a plurality of gradient vector phase values. The at least one controller is further configured to generate an estimate of a pose of the medical device in response at least in part to the plurality of gradient vector phase values. The system further comprises at least one output interface in operative communication with the at least one controller. The at least one output interface is configured to provide information regarding the estimated pose of the medical device.

In another aspect disclosed herein, a method comprises receiving a measurement set comprising a plurality of measurement values generated using a plurality of electrodes distributed along an elongate structure configured to be implanted in and/or on a body portion of a recipient. The measurement set is indicative of a pose of the elongate structure relative to the body portion. The method further comprises generating, in response at least in part to the measurement set, a gradient vector dataset comprising a plurality of gradient vector phase values. The method further comprises generating, in response at least in part to the gradient vector dataset, an evaluation of the pose of the elongate structure relative to the body portion.

In another aspect disclosed herein, a non-transitory computer readable storage medium has stored thereon a computer program that instructs a computer system to provide real-time information regarding a structure as the structure is being inserted into and/or retracted from a region. The computer system provides the real-time information by at least, in response at least in part to transimpedance or voltage measurements made while the structure is being inserted into the region and/or retracted from the region, generating a gradient vector dataset comprising a plurality of gradient vector phase values, and, using at least one processor, generating at least one estimate of the pose of the structure relative to the region, said generating based at least in part on the gradient vector dataset.

BRIEF DESCRIPTION OF THE DRAWINGS

Implementations are described herein in conjunction with the accompanying drawings, in which:

FIG. 5A schematically illustrates an example TI matrix of TI measurement values for an electrode array in an unfolded state and an example gradient vector matrix for the electrode array in an unfolded state in accordance with certain implementations described herein;

DETAILED DESCRIPTION

Figure 1:
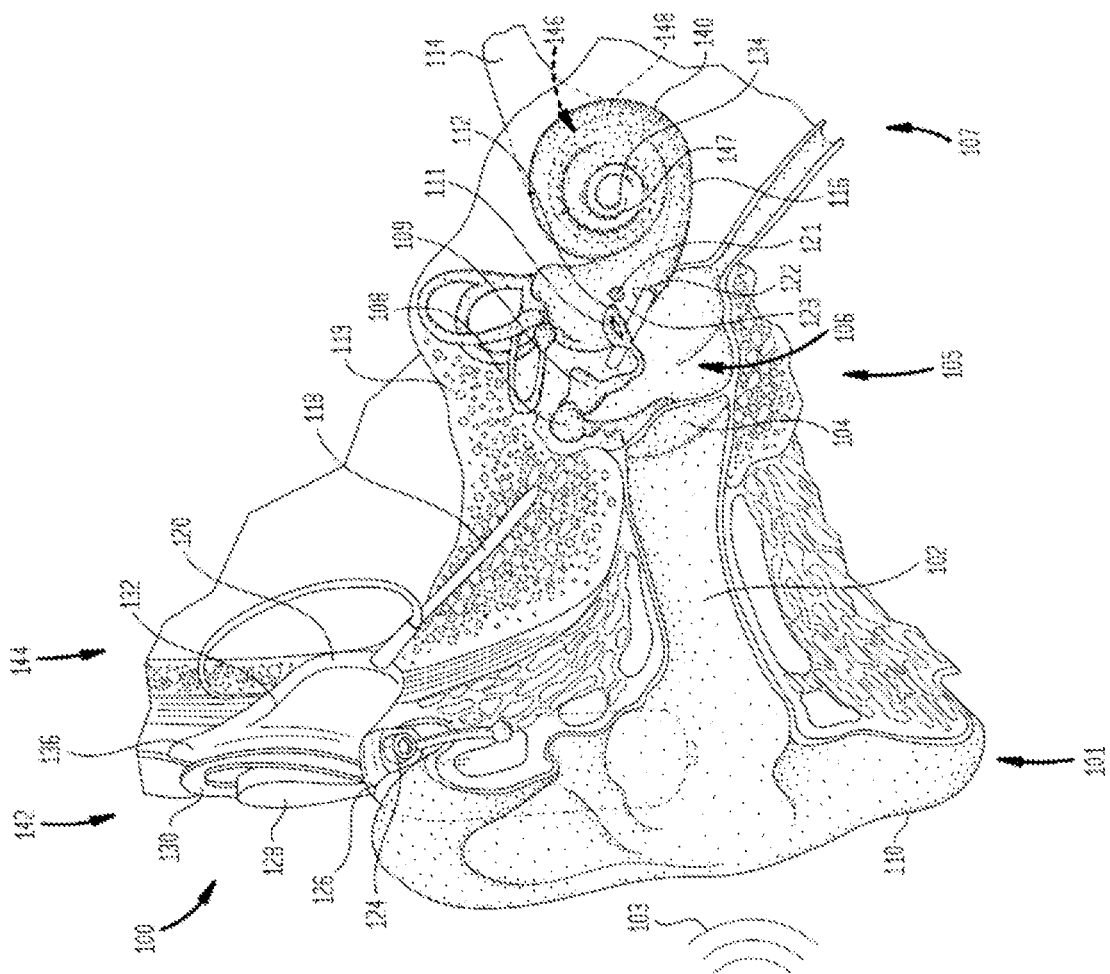
FIG. 1 is a perspective view of an example auditory prosthesis implanted in a recipient with a stimulation assembly inserted into the cochlea in accordance with certain implementations described herein.

Certain implementations described herein provide a system and method for providing medical professionals (e.g., surgeons) with real-time information (e.g., feedback) regarding the pose of a structure (e.g., electrode array of a cochlear implant system) as the structure is being implanted into a body portion (e.g., cochlea) of a recipient. Such real-time information can be advantageously used to avoid sub-optimal implantation of the structure, to provide better and more consistent outcomes for recipients, and/or to improve the surgical techniques of the medical professionals.

Certain implementations described herein utilize transimpedance measurements made (e.g., during the implantation and/or post-operatively) and a transimpedance gradient vector dataset based on the transimpedance measurements to evaluate the pose of the structure relative to the body portion. For example, the system and method can facilitate positioning of an electrode array as the array is being inserted into the cochlea by: making transimpedance measurements (e.g., during the insertion and/or intra-operatively after the insertion of the electrode has been completed to check or verify the final placement of the electrode array) that relate to the pose of the array relative to the cochlea, using the resulting transimpedance gradient vector phase values to estimate the pose of the electrode array in the cochlea, and providing feedback information regarding the estimates in real-time to the operator (e.g., via the auditory prosthesis system or an auxiliary device).

The teachings detailed herein are applicable, in at least some implementations, to any type of implantable medical device (e.g., implantable stimulation system) comprising a first portion implanted on or within the recipient's body and configured to provide stimulation signals to a portion of the recipient's body and a second portion (e.g., implanted on or within the recipient or external to the recipient's body) configured to provide control signals to the first portion. For example, the implantable medical device can comprise a sensor (e.g., auditory) prosthesis system, a neurostimulation system, or a muscle stimulation system Implementations can include any type of medical device that can utilize the teachings detailed herein and/or variations thereof.

Merely for ease of description, apparatus and methods disclosed herein are primarily described with reference to an illustrative medical device, namely a cochlear implant. However, the teachings detailed herein and/or variations thereof may also be used with a variety of other medical devices that provide a wide range of therapeutic benefits to recipients, patients, or other users. In some implementations, the teachings detailed herein and/or variations thereof can be utilized in other types of implantable medical devices beyond auditory prostheses. For example, apparatus and methods disclosed herein and/or variations thereof may also be used with one or more of the following: vestibular devices (e.g., vestibular implants); visual devices (e.g., bionic eyes); visual prostheses (e.g., retinal implants); sensors; cardiac pacemakers; drug delivery systems; defibrillators; functional electrical stimulation devices; catheters; brain implants; seizure devices (e.g., devices for monitoring and/or treating epileptic events); sleep apnea devices; electroporation; pain relief devices; swallowing treatment devices (e.g., devices for treating difficulties with the hyoglossus and/or thyrohyoid muscles); dysphagia treatment devices; devices for treating dry mouth (e.g., xerostomia or hyposalivation), devices for treating excessive or absence of muscle movement due to stroke, Parkinson's disease, or other brain disorders, devices for treating hypertension (e.g., by stimulating the carotid sinus barosensory system); etc.

FIG. 1 is a perspective view of an example auditory prosthesis 100 (e.g., cochlear implant), implanted in a recipient with a stimulation assembly 118 inserted into the cochlea 140 in accordance with certain implementations described herein. As shown in FIG. 1, the recipient has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within the cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent to the auricle 110 of the recipient). The external component 142 typically comprises one or more sound input elements (e.g., an external microphone 124) for detecting sound, a sound processing unit 126 (e.g., disposed in a Behind-The-Ear unit), a power source (not shown), and an external transmitter unit 128. In the illustrative implementation of FIG. 1, the external transmitter unit 128 comprises an external coil 130 (e.g., a wire antenna coil comprising multiple turns of electrically insulated single-strand or multi-strand platinum or gold wire) and, preferably, a magnet (not shown) secured directly or indirectly to the external coil 130. The external coil 130 of the external transmitter unit 128 is part of an inductive radio frequency (RF) communication link with the internal component 144. The sound processing unit 126 processes the output of the microphone 124 that is positioned externally to the recipient's body, in the depicted implementation, by the recipient's auricle 110. The sound processing unit 126 generates encoded signals, sometimes referred to herein as encoded data signals, which are provided to the external transmitter unit 128 (e.g., via a cable).

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate stimulation assembly 118. In some implementations, the internal receiver unit 132 and the stimulator unit 120 are hermetically sealed within a biocompatible housing, sometimes collectively referred to as a stimulator/receiver unit. The internal receiver unit 132 comprises an internal coil 136 (e.g., a wire antenna coil comprising multiple turns of electrically insulated single-strand or multi-strand platinum or gold wire), and preferably, a magnet (also not shown) fixed relative to the internal coil 136. The internal coil 136 receives power and/or data signals from the external coil 130 via a transcutaneous energy transfer link (e.g., an inductive RF link). The stimulator unit 120 generates electrical stimulation signals based on the data signals, and the stimulation signals are delivered to the recipient via the elongate stimulation assembly 118.

The elongate stimulation assembly 118 has a proximal end connected to the stimulator unit 120, and a distal end implanted in the cochlea 140. The stimulation assembly 118 extends from the stimulator unit 120 to the cochlea 140 through the mastoid bone 119. In some implementations, the stimulation assembly 118 may be implanted at least in the basal region 116, and sometimes further. For example, the stimulation assembly 118 may extend towards the apical end of the cochlea 140, referred to as the cochlea apex 134. In certain circumstances, the stimulation assembly 118 may be inserted into the cochlea 140 via a cochleostomy 122. In other circumstances, a cochleostomy 122 may be formed through the round window 121, the oval window 112, the promontory 123, or through an apical turn 147 of the cochlea 140.

The elongate stimulation assembly 118 comprises a longitudinally aligned and distally extending array 146 (e.g., electrode array; contact array) of stimulation elements 148 (e.g., electrical electrodes; electrical contacts; optical emitters; optical contacts). For example, the stimulation elements 148 can comprise intra-cochlear electrodes (ICEs) and/or extra-cochlear electrodes (ECEs). The stimulation elements 148 are longitudinally spaced from one another along a length of the elongate body of the stimulation assembly 118. For example, the stimulating assembly 118 can comprise an array 146 comprising twenty-two (22) stimulation elements 148 that are configured to deliver stimulation to the cochlea 140. Although the array 146 of stimulation elements 148 can be disposed on the stimulation assembly 118, in most practical applications, the array 146 is integrated into the stimulation assembly 118 (e.g., the stimulation elements 148 of the array 146 are disposed in the stimulation assembly 118). As noted, the stimulator unit 120 generates stimulation signals (e.g., electrical signals; optical signals) which are applied by the stimulation elements 148 to the cochlea 140, thereby stimulating the auditory nerve 114.

A variety of types of intra-cochlear stimulation assemblies 118 are compatible with certain embodiments described herein, including but not limited to: short, straight, and perimodiolar. A perimodiolar stimulation assembly 118 is configured to adopt a curved configuration during and/or after implantation into the cochlea 140. To achieve this, in certain implementations, the perimodiolar stimulation assembly 118 is pre-curved to the same general curvature of the cochlea 140. Such examples of the stimulation assembly 118 can be held straight by, for example, a stiffening stylet (not shown) or sheath which is removed during implantation, or alternatively varying material combinations or the use of shape memory materials, so that the stimulation assembly 118 may adopt its curved configuration when in the cochlea 140. Other methods of implantation, as well as other stimulation assemblies 118 which adopt a curved configuration, may be used. The stimulation assembly 118 of certain other implementations comprises a non-perimodiolar stimulation assembly 118. For example, the stimulation assembly 118 can comprise a straight stimulation assembly 118 or a mid-scala assembly which assumes a mid-scala position during or following implantation. Alternatively, the stimulation assembly 118 can comprise a short electrode implanted into at least the basal region of the cochlea 140.

Figure 2:
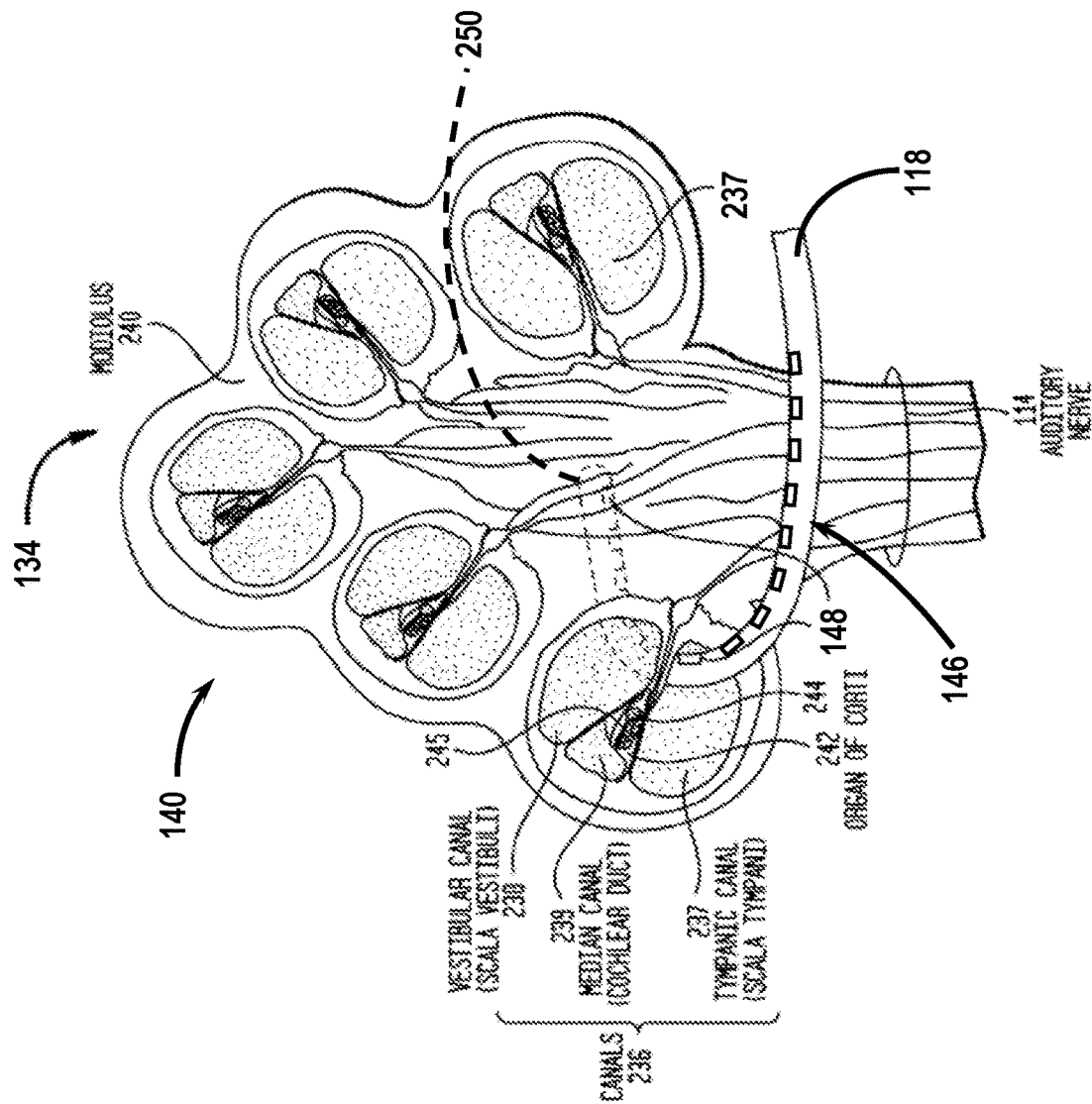
FIG. 2 is cross-sectional view of the cochlea illustrating the stimulating assembly partially implanted therein in accordance with certain implementations described herein.

FIG. 2 is cross-sectional view of the cochlea 140 illustrating the stimulating assembly 118 partially implanted therein in accordance with certain implementations described herein. Only a subset of the stimulation elements 148 of the stimulation assembly 118 is shown in FIG. 2. The cochlea 140 is a conical spiral structure that comprises three parallel fluid-filled canals or ducts, collectively and generally referred to herein as canals 236. Canals 236 comprise the tympanic canal 237, also referred to as the scala tympani 237, the vestibular canal 238, also referred to as the scala vestibuli 238, and the median canal 239, also referred to as the scala media 239. The cochlea 140 includes the modiolus 240 which is a conical shaped central region around which the cochlea canals 236 spiral. The modiolus 240 consists of spongy bone in which the cochlea nerve cells, sometimes referred to herein as the spiral ganglion cells, are situated. The cochlea canals 236 generally turn 2.5 times around modiolus 240.

In normal hearing, sound entering the auricle 110 (see, e.g., FIG. 1) causes pressure changes in the cochlea 140 that travel through the fluid-filled tympanic and vestibular canals 237, 238. The organ of Corti 242, which is situated on the basilar membrane 244 in scala media 239, contains rows of hair cells (not shown) which protrude from its surface. Located above the hair cells is the tectoral membrane 245 which moves in response to pressure variations in the fluid-filled tympanic and vestibular canals 237, 238. Small relative movements of the layers of the tectoral membrane 245 are sufficient to cause the hair cells to move, thereby causing the creation of a voltage pulse or action potential which travels along the associated nerve fibers that connect the hair cells with the auditory nerve 114. The auditory nerve 114 relays the impulses to the auditory areas of the brain (not shown) for processing.

Typically, in cochlear implant recipients, some portion of the cochlea 140 (e.g., the hair cells) is damaged such that the cochlea 140 cannot transduce pressure changes into nerve impulses for relay to the brain. As such, the stimulating elements 148 of the stimulating assembly 118 are used to directly stimulate the cells to create nerve impulses resulting in perception of a received sound (e.g., to evoke a hearing precept).

To insert the intra-cochlear stimulating assembly 118 into the cochlea 140, an opening (facial recess) is created through the recipient's mastoid bone 119 (see, e.g., FIG. 1) to access the recipient's middle ear cavity 106 (see, e.g., FIG. 1). An opening is then created from the middle ear 106 into the cochlea 140 through, for example, the round window 121, oval window 112, the promontory 123, etc. of the cochlea 140. The stimulating assembly 118 is then gently advanced (e.g., pushed) forward into the cochlea 140 until the stimulating assembly 118 achieves the implanted position. As shown in FIGS. 1 and 2, the stimulating assembly 118 follows the helical shape of the cochlea 140. That is, the stimulating assembly 118 spirals around the modiolus 240.

The effectiveness of the stimulation by the stimulation assembly 118 depends, at least in part, on the place along the basilar membrane 244 where the stimulation is delivered. That is, the cochlea 140 has characteristically been referred to as being "tonotopically mapped," in that regions of the cochlea 140 toward the basal end are more responsive to high frequency signals, while regions of cochlea 140 toward the apical end are more responsive to low frequency signals. These tonotopical properties of the cochlea 140 are exploited in a cochlear implant by delivering stimulation within a predetermined frequency range to a region of the cochlea 140 that is most sensitive to that particular frequency range. However, this stimulation relies on the particular stimulation elements 148 having a final implanted positioned adjacent to a corresponding tonotopic region of the cochlea 140 (e.g., a region of the cochlea 140 that is sensitive to the frequency of sound represented by the stimulation element 148).

To achieve a selected final implanted position, the apical (e.g., distal end/tip) portion 250 of the array 146 is placed at a selected angular position (e.g., angular insertion depth). As used herein, the angular position or angular insertion depth refers to the angular rotation of the apical portion 250 of the array 146 from the cochleostomy 122 (e.g., round window 121) through which the stimulation assembly 118 enters the cochlea 140. As such, the angular position/angular insertion depth may be expressed in terms of how many angular degrees the apical portion 250 has traveled within the cochlea 140 with respect to the cochleostomy 122. For example, an angular insertion depth of one hundred and eighty (180) degrees indicates that the apical portion 250 has traveled around half (½) of the first turn of the cochlea 140. An angular insertion depth of three hundred and sixty (360) degrees indicates that the apical portion 250 has traveled completely around the first turn of the cochlea 140.

In certain implementations, while the stimulation assembly 118 is being implanted (e.g., during a surgical procedure conducted by an operator, such as a medical professional, surgeon, and/or an automated or robotic surgical system), a location and/or an orientation of the array 146 relative to the cochlea 140 (e.g., collectively referred to as the pose of the array 146) is adjusted as the array 146 is advanced and placed into position within the cochlea 140. The goal of the implantation is that the fully-implanted array 146 has an optimal pose in which the array 146 is positioned such that the stimulation elements 148 are adjacent to the corresponding tonotopic regions of the cochlea 140. To achieve the optimal pose, the array 146 is expected to follow a trajectory in the cochlea 140 whereby (i) the stimulation elements 148 are distributed linearly along an axis of the cochlear duct 239, (ii) the array 146 does not make contact with the basilar membrane 244, and (iii) the stimulation elements 148 are in close proximity to the modiolar wall (e.g., if the array 146 is pre-curved) or the stimulation elements 148 are distant from the modiolar wall (e.g., if the array 146 is not pre-curved).

However, one or more these expectations may be violated during insertion of the array 146. For example, the apical portion 250 of the array 146 can become snagged on the wall of the cochlear duct 239, the array 146 can become buckled, folded, and/or overinserted, and/or portions of the cochlea 140 (e.g., scala tympani 237; scala vestibuli 238; cochlear duct 239; organ of Corti 242; basilar membrane 244) can be dislocated, resulting in sub-optimal placement of the array 146. It is desirable to provide the operator with information regarding the pose and/or state of the array 146 (e.g., feedback information provided in real-time during the implantation process). For example, metrics related to the pose of the array 146 (e.g., existence and position of foldover) can be reported continuously, at predetermined intervals, and/or in response to requests by the operator, and alerts regarding events related to insertion (e.g., snagged electrode; other non-optimal conditions) can be provided to the operator, so the operator can take corrective measures.

Figures 3A, 3B, 3C:
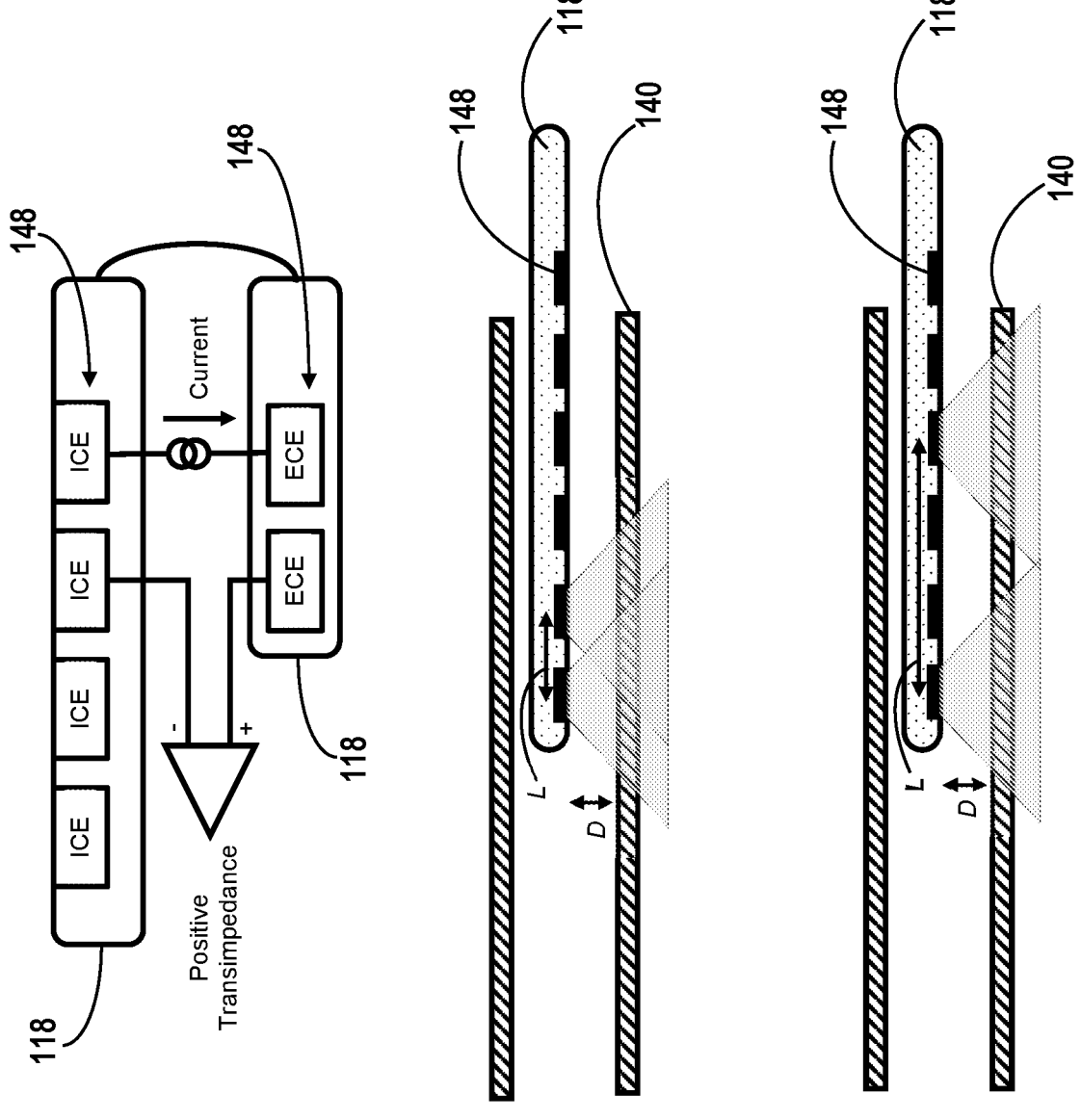
FIGS. 3A-3C schematically illustrate example transimpedance (TI) measurements that can be made using a plurality of transducers of at least a portion of a medical device in and/or on a body portion of the recipient in accordance with certain implementations described herein.

FIGS. 3A-3C schematically illustrate example transimpedance (TI) measurements that can be made using a plurality of transducers (e.g., electrodes) of at least a portion of a medical device in and/or on a body portion of the recipient in accordance with certain implementations described herein. For example, the medical device can comprise a stimulation assembly 118 of a cochlear implant auditory prosthesis 100, the body portion can comprise a cochlea 140 of the recipient, and the TI measurements can be made using an array 146 of electrodes 148 of the stimulation assembly 118. The TI measurements can be used to generate a TI measurement set comprising a plurality of TI measurement values in accordance with certain implementations described herein.

The TI measurement values can be measured between electrodes 148 inside the cochlea 140 (e.g., intra-cochlear electrodes or ICEs) and/or electrodes 148 outside the cochlea 140 (e.g., extra-cochlear electrodes or ECEs) before, during, and/or after electrical stimulation (e.g., production of electrical current between electrodes 148) of the cochlea 140 by the electrodes 148 and/or during or after implantation of at least a portion of the medical device in and/or on the body portion of the recipient. For example, FIG. 3A schematically illustrates TI measurements made between an ICE and an ECE, FIG. 3B schematically illustrates TI measurements made between a first ICE and a second ICE adjacent to the first ICE, and FIG. 3C schematically illustrates TI measurements made between the first ICE and a third ICE that is not adjacent to the first ICE.

FIG. 3A schematically illustrates an example polarity convention for the TI measurements in accordance with certain implementations described herein. For at least one electrode 148 (e.g., for each electrode 148), transimpedances can be measured as positive values or as negative values (e.g., in ohms) dependent on the orientation of the recording amplifier with respect to the current flow in the tissue. For TI measurements between at least one pair of electrodes (e.g., for each possible pair of electrodes 148), a current can be applied to a stimulation pair of electrodes and a voltage can be detected across a measurement pair of electrodes. In certain implementations, a subset of the stimulating electrodes is shared with a subset of the recording electrodes.

In certain implementations, the TI measurement values are sensitive to the modiolar proximity D of each of the two electrodes 148 and/or to the distance L between the two electrodes 148 in the cochlea 140. For example, TI measurement values vary with the distance L between the stimulation electrode and the measurement electrode, and such voltage measurements can be used to produce a transimpedance matrix (TIM) comprising an array of cells (e.g., TIM cells) comprising TI measurement values. As the distance L increases (compare the shorter distance L between two adjacent electrodes 148, as shown in FIG. 3B to the longer distance L between non-adjacent electrodes 148, as shown in FIG. 3C), the voltage V detected by the measurement electrode decreases, hence the corresponding values of the TIM decrease. For example, TI measurements can be used for classifying electrode pose (e.g., whether the electrode is folded over or not; the location of the folded over electrode portion) (see, e.g., U.S. Pat. Appl. Publ. No. 2018/0140829). In addition, voltage recordings taken using one or more electrodes 148 in the cochlea 140 during electrical stimulation vary with the extent of immersion of the electrode 148 in the cochlear duct 239, due to the ability for electrical current to flow from the electrode 148 (see, e.g., U.S. Pat. No. 9,987,490).

In certain implementations, the TI measurement set is indicative of symmetric changes in the pose of the structure (e.g., the changes at each point of the structure are the same as one another) during insertion and/or retraction of the structure relative to the body portion. In certain other implementations, the TI measurement set is indicative of asymmetric changes in the pose of the structure (e.g., the changes at two or more points of the structure are different from one another) during insertion and/or retraction of the structure relative to the body portion. For example, asymmetric changes can occur during insertion and/or retraction when the base of the electrode array moves while the apex of the electrode array does not move.

Figure 4A:
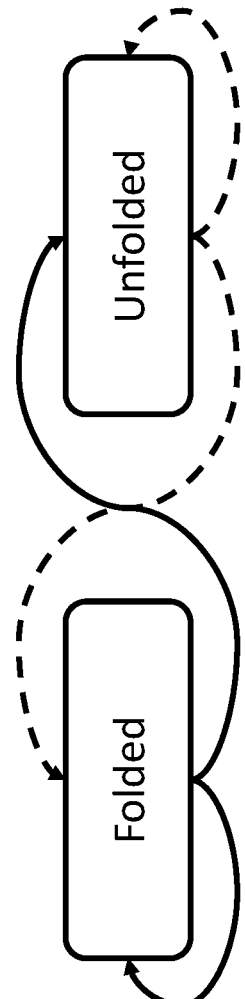
FIGS. 4A-4C schematically illustrate an example model of the structure and/or the body portion in accordance with certain implementations described herein.
Figures 4B, 4C:
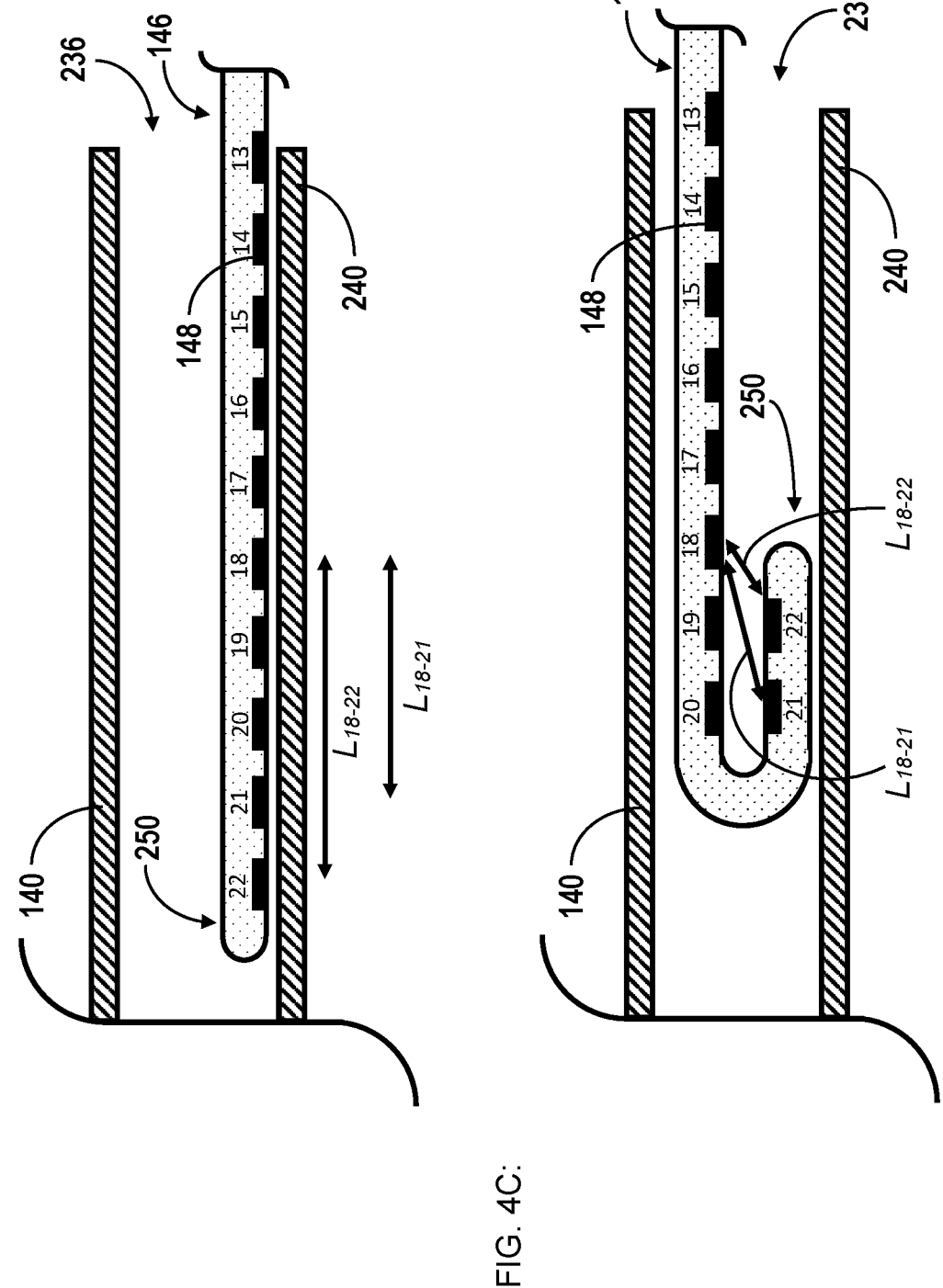

FIGS. 4A-4C schematically illustrate an example model of the structure and/or the body portion in accordance with certain implementations described herein. The example of FIGS. 4A-4C is applicable to detection of a folded state of an apical portion 250 of an electrode array 146. FIG. 4A illustrates an example state diagram with two states for an electrode array 146 (e.g., a pre-curved electrode array 146) being inserted into a cochlea 140. In an "unfolded" state (e.g., alternatively referred to as a "modiolar-proximal" or "modiolar-hugging" state), as schematically illustrated by FIG. 4B), the electrode array 146 extends in a single direction along the canals 236 (e.g., is optimally positioned relative to the electrode base or modiolus 240). In a "folded" state, schematically illustrated by FIG. 4C, at least a portion of the electrode array 146 extends away from the electrode base and the apical portion 250 extends towards the modiolus 240, with an acute angle (e.g., bend; kink) between the two portions. In certain other implementations, the model can include a third (e.g., intermediate) state for the electrode array 146, between the "unfolded" state and the "folded" state, in which a portion of the electrode array 146 extends away from the electrode base and the apical portion 250 extends towards the modiolus 240, with an obtuse angle (e.g., bend; kink) between the two portions (e.g., referred to as a "snagged" state).

As shown in FIG. 4A, the pose of the electrode array 146 can transition (e.g., from a time $t_1$ to a time $t_2 > t_1$) among the states of the model during insertion into the cochlea 140 (e.g., while advancing the electrode array 146 apically into the cochlea 140 and/or withdrawing the electrode array 146 basally from the cochlea 140). For example, for the two-state model of FIG. 4A, from the "unfolded" state, the electrode array 146 can either remain in the "unfolded" state (e.g., inserted deeper into the cochlea 140) or can transition to the "folded" state. From the "folded" state, the electrode array 146 can either remain in the "folded" state or can transition to the "unfolded" state. For a model further comprising the "snagged" state between the "unfolded" state and the "folded" state, the electrode array 146 in the "unfolded" state can either remain in the "unfolded" state or can transition to the "snagged" state, the electrode array 146 in the "snagged" state can remain in the "snagged" state, transition to the "folded" state, or transition to the "unfolded" state, and the electrode array 146 in the "folded" state can remain in the "folded" state or can transition to the "snagged" state.

In certain implementations, each of the states of the model describes a collection of poses of the electrode array 146 that affect the TI measurement values from the electrodes 148. For example, referring to FIG. 4B, the "unfolded" state can describe a collection of poses in which the distance $L_{18\text{-}22}$ between electrode 18 and electrode 22 is greater than the distance $L_{18\text{-}21}$ between electrode 18 and electrode 21 and the uncorrected transimpedance $Z_{18\text{-}22}$ between electrode 18 and electrode 22 (used in measuring and calculating the TIM) is expected to be less than the uncorrected transimpedance $Z_{18\text{-}21}$ between electrode 18 and electrode 21 because there is less current passing through this region when the stimulating electrode 18 is more distant as the generated electric field that reaches electrode 22 is lower than the generated electric field that reaches electrode 21. However, calculating a corrected transimpedance which would take into account the electric field decay with distance (e.g., using an a priori geometry of the electrode array and cochlear microstructure), the corrected transimpedance $Z_{18\text{-}22}$ between electrode 18 and electrode 22 would be larger than the corrected transimpedance $Z_{18\text{-}21}$ between electrode 18 and electrode 21. Conversely, referring to FIG. 4C, the "folded" state can describe a collection of poses in which the distance $L_{18\text{-}21}$ between electrode 18 and electrode 21 is greater than the distance $L_{18\text{-}22}$ between electrode 18 and electrode 22 and the uncorrected transimpedance $Z_{18\text{-}22}$ between electrode 18 and electrode 22 is expected to be greater than the uncorrected transimpedance $Z_{18\text{-}21}$ between electrode 18 and electrode 21.

Figure 5A:
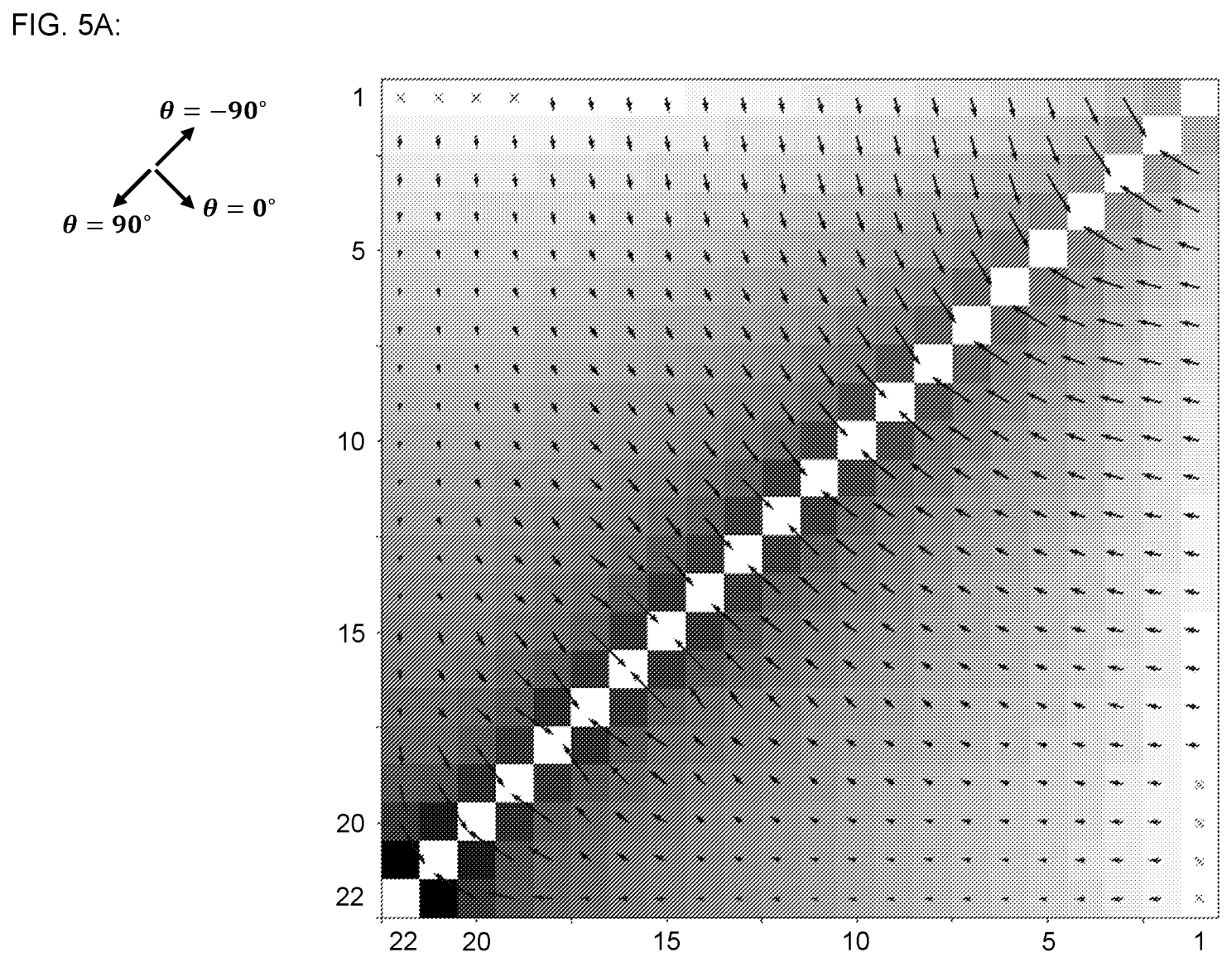
Figure 5B:
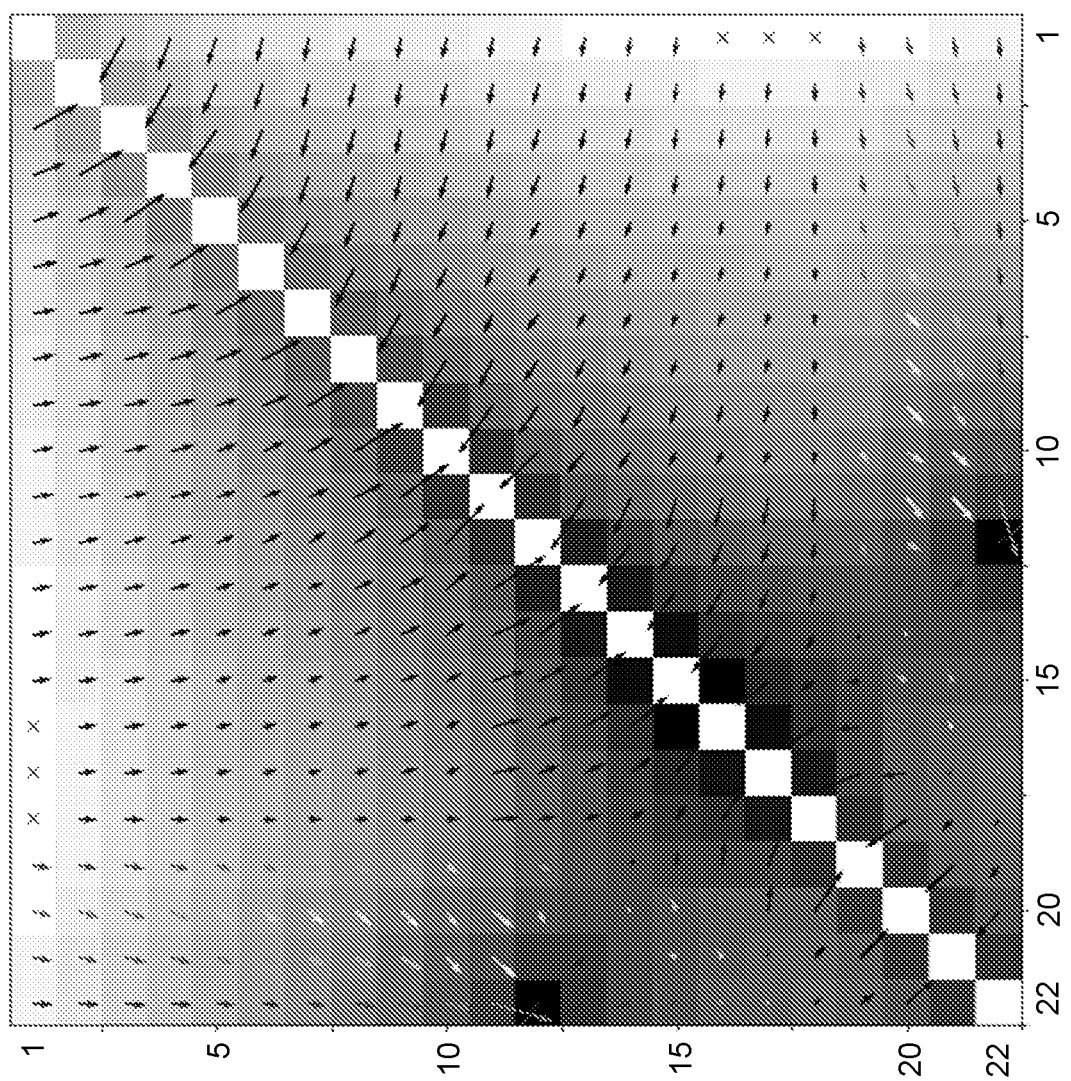
FIG. 5B schematically illustrates an example transimpedance matrix of TI measurement values for an electrode array in a folded state and an example gradient vector matrix for the electrode array in the folded state in accordance with certain implementations described herein.

FIG. 5A schematically illustrates an example TI matrix of TI measurement values for an electrode array 146 in an unfolded state in accordance with certain implementations described herein. FIG. 5B schematically illustrates an example TI matrix of TI measurement values for the electrode array 146 in a folded state in accordance with certain implementations described herein. The TI matrices of FIGS. 5A and 5B comprise TI measurement values for an electrode array 146 comprising 22 electrodes, and the shading of each cell at row x and column y (e.g., matrix cell TIM(x; y)) is indicative of the magnitude of the voltage detected at electrode y during monopolar stimulation of electrode x, divided by the current applied through electrode x, with darker cells indicative of larger TI measurement values. In the TI matrices of FIGS. 5A and 5B, the diagonal cells are blank (e.g., TIM(x=y)=0), and the TI measurement values for pairs of electrodes that are closer together are generally larger than the TI measurement values for pairs of electrodes that are farther away from one another. While each of the TI matrices of FIGS. 5A and 5B is substantially symmetric (e.g., each matrix cell TIM(x; y) is substantially equal to its reciprocal matrix cell TIM(y; x)), other TI matrices can be asymmetric (e.g., at least some matrix cells TIM(x; y) are not substantially equal to the reciprocal matrix cells TIM(y; x)). While the magnitudes and patterns observed in the TI measurement values can be used to provide information indicative of the folded or unfolded state of the electrode array 146, such comparisons can be difficult to incorporate in an automated evaluation.

In certain implementations, a gradient vector comprising a magnitude and a phase is calculated for at least some of the cells of the TI matrix, using the TI measurement values of neighboring cells. FIG. 5A schematically illustrates an example gradient vector (GV) matrix for the electrode array in an unfolded state in accordance with certain implementations described herein. FIG. 5B schematically illustrates an example GV matrix for the electrode array in the folded state in accordance with certain implementations described herein. The magnitudes and directions of the arrows of the GV matrices of FIGS. 5A and 5B are indicative of the magnitudes and phases, respectively, of the gradient vectors of the various cells. FIG. 5A includes an example coordinate system for describing the GV phase in a TI matrix in which gradient vectors perpendicular to the main diagonal of the TI matrix are defined to have a phase of zero, gradient vectors pointing towards the apical electrodes are positive, and all phases line in the interval −180 degrees to +180 degrees. Other coordinate systems are also compatible with certain implementations described herein.

The GV matrices of unfolded electrode arrays 146, as schematically illustrated in FIG. 5A, have a characteristic pattern which is different from the patterns of GV matrices of folded electrode arrays 146, as schematically illustrated by FIG. 5B. For example, for a folded electrode array 146, nearby electrodes can be identified by a cross-diagonal of large TI values that runs perpendicular to the main diagonal of the TI matrix, and this same cross-diagonal can be identified by large absolute gradient phase values of the GV matrix. As schematically illustrated by FIG. 5B, at least some of the cells of the GV matrix for the electrode array 146 in a folded state have large absolute gradient phase values, while in certain implementations, the cells of the GV matrix for the electrode array 146 in the unfolded state have gradient phase values that do not generally exceed 45 degrees. In certain implementations described herein, a gradient phase range is used as a metric to distinguish between the unfolded and folded states of the electrode array 146. In addition, in certain implementations, the apex of a folded electrode array 146 can be determined by identifying an intersection in the TI matrix and/or the GV matrix of the cross-diagonal with the main diagonal.

Figure 6:
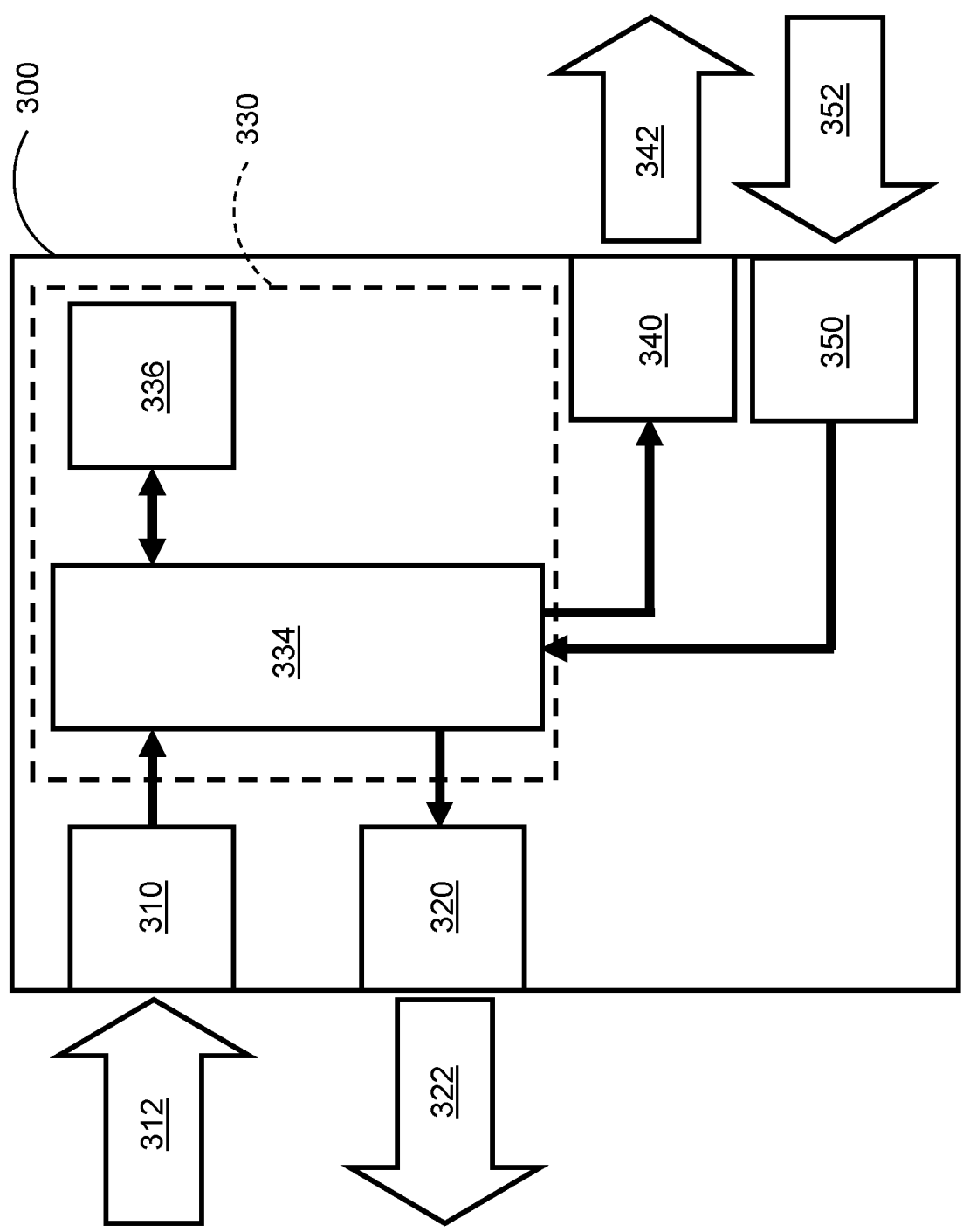
FIG. 6 schematically illustrates an example system in accordance with certain implementations described herein.

FIG. 6 schematically illustrates an example system 300 in accordance with certain implementations described herein. The system 300 comprises at least one data input interface 310 configured to receive data 312 from a plurality of electrodes 148 of a medical device (e.g., during and/or after implantation of the medical device on or in a body portion of a recipient). The system 300 further comprises at least one control output interface 320 configured to transmit control signals 322 to the plurality of electrodes 148. The plurality of electrodes 148 is responsive to the control signals 322 by generating the data 312. The system 300 further comprises at least one controller 330 in operative communication with the at least one data input interface 310 and the at least one control output interface 320. The at least one controller 330 is configured to generate an estimate of a pose of the medical device in response at least in part to the received data 312. The system 300 further comprises at least one output interface 340 in operative communication with the at least one controller 330 and configured to provide information 342 regarding the estimated pose of the medical device. In certain implementations, the system 300 further comprises at least one user input interface 350 in operative communication with the at least one controller 330 and configured to provide user input 352 to the at least one controller 330.

In certain implementations, the system 300 comprises at least one computing device configured to be in operative communication with the plurality of electrodes 148 (e.g., via the at least one data input interface 310 and the at least one control output interface 320) and in operative communication (e.g., via the at least one output interface 340 and the at least one user input interface 350) with an operator (e.g., medical professional; surgeon; automated or robotic surgical system). The at least one computing device can include, but is not limited to: a desktop computer, a laptop computer, a mobile computing device or accessory; a smartphone; a smart tablet. The at least one computing device can be in communication with another computing device (e.g., via the at least one output interface 340 and/or the at least one user input interface 350) that is being utilized by the operator (e.g., an external device being used by a medical professional or surgeon; a component of the automated or robotic surgical system). In certain implementations, the at least one computing device is external to the implantable medical device, while in certain other implementations, the at least one computing device is incorporated in the implantable medical device.

The at least one data input interface 310, the at least one control output interface 320, the at least one output interface 340, and/or the at least one user input interface 350 can comprise any combination of wired and/or wireless ports, including but not limited to: Universal Serial Bus (USB) ports; Institute of Electrical and Electronics Engineers (IEEE) 1394 ports; PS/2 ports; network ports; Ethernet ports; Bluetooth ports; wireless network interfaces. In certain implementations, the at least one data input interface 310 and the at least one control output interface 320 are integral with one another (e.g., comprising the same ports as one another), while in certain other implementations, the at least one data input interface 310 and the at least one control output interface 320 are separate from one another.

The at least one output interface 340 of certain implementations is configured to be in operative communication with at least one communication device (e.g., display device; screen; status indicator light; audio device; speaker; vibration motor) configured to communicate information to the operator (e.g., during the implantation of the medical device). For example, the at least one communication device can provide information, alerts, and/or alarms to the operator regarding the pose of the medical device and/or regarding the operative status of the system 300. The at least one user input interface 350 can be configured to be in operative communication with one or more keyboard, computer mouse, touchscreen, switches, buttons, or other devices with which a human operator (e.g., medical professional; surgeon) can provide the system 300 with commands or data.

In certain implementations, the at least one controller 330 is configured to transmit the control signals 322 to the plurality of electrodes 148 automatically (e.g., at a predetermined constant repetition rate; at times determined by the internal logic of the controller 330) during and/or after the implantation of the medical device. For example, the plurality of electrodes 148 can be activated or triggered to perform data collection automatically upon connection of the system 300 to the plurality of electrodes 148 of the medical device (e.g., connection of a surgical sound processing unit 126 to a cochlear implant system 100 during implantation). In certain other implementations, the at least one controller 330 is configured to receive triggering signals from the at least one user input interface 350 intermittently during and/or after the implantation of the medical device. The at least one controller 330 can be configured to respond to the triggering signals by transmitting the control signals 322 to the plurality of electrodes 148. In this way, the plurality of electrodes 148 can be selectively activated by the human operator (e.g., by pressing a button of an external device in operative communication with the at least one user input interface 350) and/or the automated or robotic surgical system. In certain other implementations, the controller 300 does not send control signals 322 to the plurality of electrodes 148 and the system 300 does not comprise a control output interface 320.

In certain implementations, the at least one controller 330 comprises at least one processor 334 and at least one storage device 336 in operative communication with the at least one processor 334. The at least one storage device 336 can be configured to collect and store the data 312 received from the plurality of electrodes 148, and the at least one processor 334 can be configured to generate the estimate of the pose of the medical device in response at least in part to the stored data. The at least one processor 334 can comprise a microprocessor or microcontroller configured to receive data 312 (e.g., TI measurement values; common ground impedance measurement values) via the at least one data input interface 310 and to transmit the received data 312 to the at least one storage device 336. The at least one processor 334 can also be configured to access the data 312 (e.g., stored on the at least one storage device 336), to generate a TI gradient vector dataset comprising a plurality of TI gradient vector phase values (e.g., and to store at least a portion of the generated TI gradient vector dataset on the at least one storage device 336), to execute instructions (e.g., stored on the at least one storage device 336), and to generate and provide information (e.g., regarding the estimated pose of the medical device) to the at least one output interface 340 and/or to the at least one storage device 336 to be stored and later retrieved.

In certain implementations, the at least one processor 334 is configured to filter the data 312 received from the plurality of electrodes 148. For example, the at least one processor 334 can filter (e.g., in the time domain; using a median filter; using an exponentially weighted moving average filter) the data 312 generated by multiple measurements. For another example, the at least one processor 334 can apply more weighting to more recently generated data 312 (e.g., to selectively apply more weighting to data 312 potentially affected by the presence of the electrode 148 in the cochlea 140). In certain implementations, the at least one processor 334 is configured to aggregate the data 312 generated by an electrode (e.g., aggregating the last 10 measurements by an electrode). In certain implementations, the at least one processor 334 is configured to aggregate the data 312 generated by multiple electrodes (e.g., aggregating the last 10 measurements by electrodes when each of the electrodes is at a predetermined location relative to the body portion in which the medical device is being implanted, such as 5 mm from the round window 121 of the cochlea 140).

In certain implementations, the at least one processor 334 is configured to associate the data 312 to particular electrodes based on prior knowledge of the configuration of the electrode array 146 used for measurement collection. For example, data 312 can be associated to a position of an electrode 148 in the cochlea 140 using a prior estimate of the pose of the electrode array 146. In certain implementations, the at least one processor 334 is configured to extrapolate the data 312 to nearby locations using interpolation (e.g., inverse distance weighted; piecewise linear interpolation).

The at least one storage device 336 can comprise at least one tangible (e.g., non-transitory) computer readable storage medium, examples of which include but are not limited to: read only memory (ROM); random access memory (RAM); magnetic disk storage media; optical storage media; flash memory. The at least one storage device 336 can be encoded with software (e.g., a computer program downloaded as an application) comprising computer executable instructions for instructing a computer system (e.g., measurement logic and/or evaluation logic to be executed by the at least one processor 334). For example, the measurement logic can be executed by the at least one processor 334 to generate the control signals 322 that activate and/or otherwise control the plurality of electrodes 148. For another example, the evaluation logic can be executed by the at least one processor 334 to evaluate the data 312 received from the plurality of electrodes 148, to generate estimates of the pose of the medical device, and to provide the information 342 regarding the estimated pose of the medical device.

Figure 7:
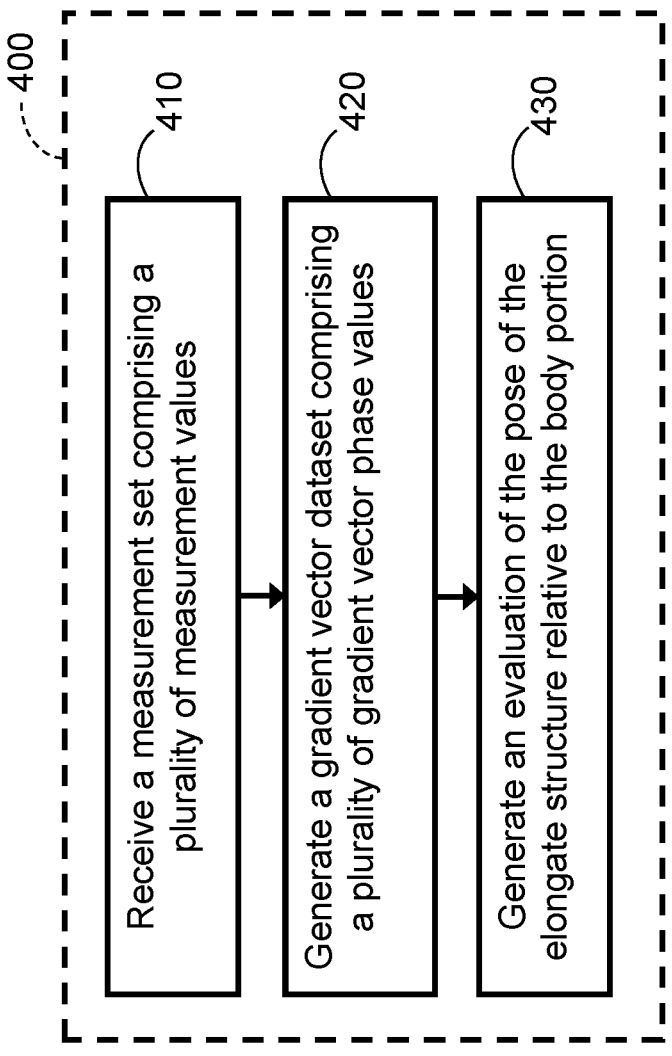
FIG. 7 is a flow diagram of an example method in accordance with certain implementations described herein.

FIG. 7 is a flow diagram of an example method 400 in accordance with certain implementations described herein. In an operational block 410, the method 400 comprises receiving a measurement set comprising a plurality of measurement values. The measurement set can be generated and received during and/or after implantation of at least a portion of the elongate structure in and/or on (e.g., into) a body portion of a recipient. In an operational block 420, the method 400 further comprises generating, in response at least in part to the measurement set, a gradient vector dataset comprising a plurality of gradient vector phase values. In an operational block 430, the method 400 further comprises generating, in response at least in part to the gradient vector dataset, an evaluation of the pose of the elongate structure relative to the body portion. In certain implementations, in an operational block 440, the method 400 further comprises communicating the evaluation, in real-time (e.g., during the implantation), to either a user (e.g., an operator of an insertion system being used for the implantation) or an automated surgical system performing the implantation.

Figure 8:
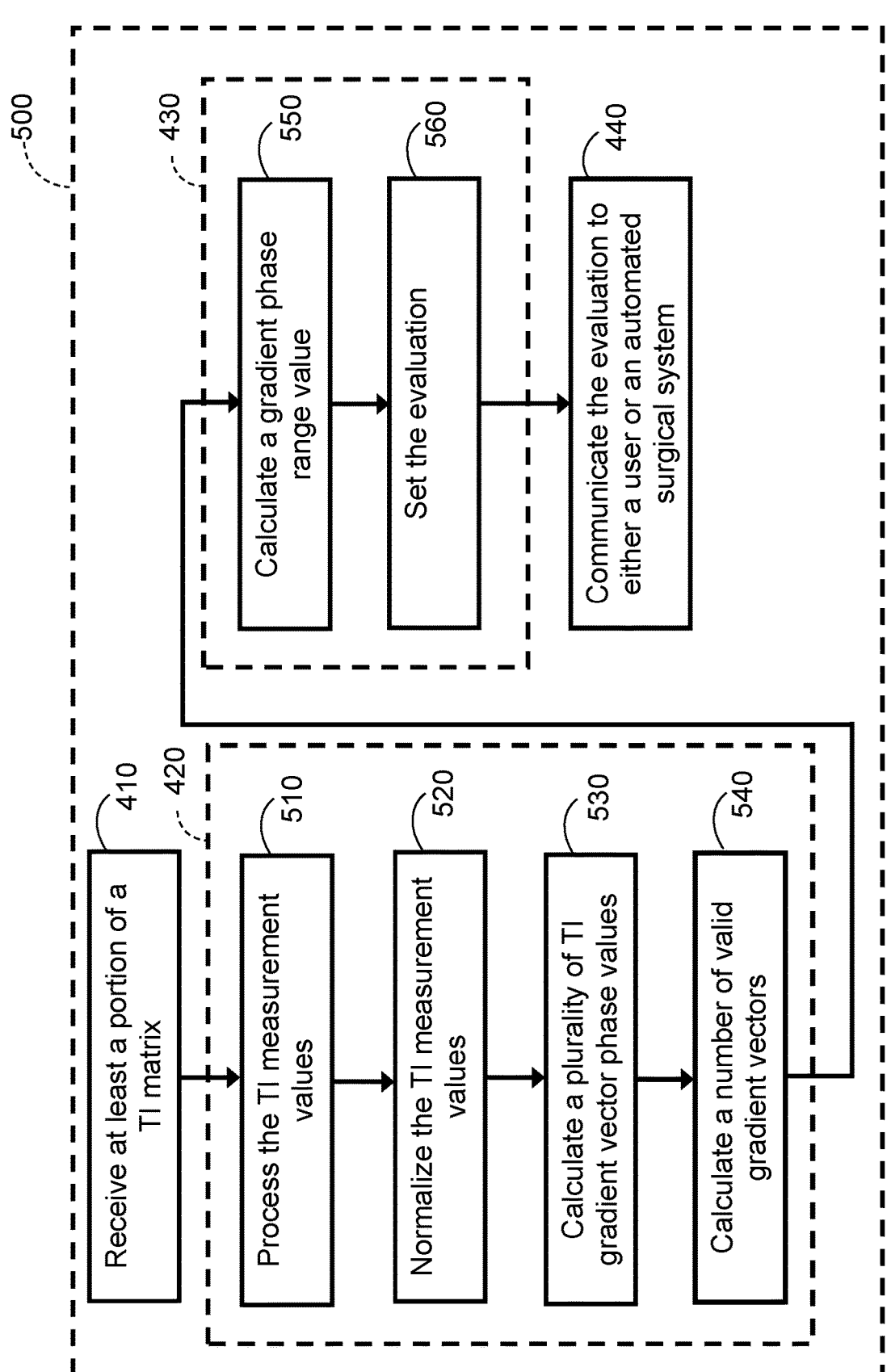
FIG. 8 is a flow diagram of an example method in accordance with certain implementations described herein.

FIG. 8 is a flow diagram of an example method 500 in accordance with certain implementations described herein. The method 500 of FIG. 8 is an example of the method 400 of FIG. 7. While certain implementations are described herein in which the plurality of measurement values comprises transimpedance (TI) measurement values and the plurality of gradient vector phase values comprises TI gradient vector phase values, in certain other implementations, the plurality of measurement values can comprise a plurality of voltage measurement values and the plurality of gradient vector phase values can comprise voltage gradient vector phase values.

In certain implementations, receiving the TI measurement set in the operational block 410 comprises receiving at least a portion of a TI matrix having TI measurement values that are generated using a plurality of electrodes (e.g., electrodes 148) distributed along an elongate structure (e.g., stimulation assembly 118) and the TI matrix is indicative of a pose of the elongate structure relative to the body portion (e.g., whether the elongate structure is in a folded state, in an unfolded state, and/or in an intermediate or snagged state between the unfolded state and the folded state). In certain implementations, for a stimulation assembly 118 comprising 22 electrodes, the TI measurement set comprises a full TI matrix of 462 TI measurement values in a 22-by-22 array (see, e.g., FIGS. 5A and 5B). In certain other implementations, the TI measurement set comprise a subset (e.g., portion) of the 22-by-22 array of TI measurement values. For example, the received TI measurement set can comprise only one half of the full TI matrix (e.g., the triangle of TIM cells above the diagonal; the triangle of TIM cells below the diagonal), two or more full rows of cells (e.g., two or more rows of cells TIM(x=1-22; y≠x); two or more full columns of cells (e.g., two or more columns of cells TIM(x≠y; y=1-22), or other sub-regions of the TI matrix.

In certain implementations, generating the TI gradient vector dataset in the operational block 420 comprises processing (e.g., filtering) the TI measurement values in the operational block 510. TI measurement values can suffer from systematic measurement artifacts (e.g., affected by issues unrelated to the presence of a foldover of the elongate structure) that can confound evaluation (e.g., estimation; determination; classification) of the pose (e.g., foldover status) of the elongate structure (e.g., due to an abnormal electrode-tissue interface or due to the presence of abnormal current paths). The processing of the TI measurement values can be performed prior to subsequent analysis (e.g., pre-processing) or as part of the subsequent analysis, and can be configured to exclude TI measurement values that are affected by such abnormalities from influencing the evaluation of the pose of the elongate structure (e.g., to mitigate the possibility of false alarms of folded status).

In certain implementations, processing (e.g., filtering) the TI measurement values can comprise removing one or more TI measurement values from the TI measurement set, the removed one or more TI measurement values comprising TI measurement values generated using at least one electrode having either an abnormal interface with tissue of the body portion or a short circuit to ground. For example, TI measurement values in cells of the TI matrix can be excluded from further analysis if one or more of the following conditions are true:

the stimulating electrode has an abnormal electrode-tissue interface, the recording electrode has an abnormal electrode-tissue interface, the stimulating electrode and the recording electrode straddle an electrode that is short circuited to ground (e.g., if electrode #10 is short circuited to ground, then cells TIM($x \geq 10$; $y \leq 10$) and cells TIM($x \leq 10$; $y \geq 10$) are excluded), or the stimulating electrode and/or the recording electrode is between two electrodes short circuited to ground (e.g., if electrodes #10 and #13 are both short circuited to ground, then cells TIM($x=11$ or 12; $y=11$ or 12) are excluded).

In certain implementations, excluded measurement data can be interpolated from other measurements since the electrodes are located in and measuring the same environment.

In certain implementations, the method 500 further comprises receiving (e.g., during the implantation) a common ground impedance (CGI) measurement set comprising CGI measurement values generated using the plurality of electrodes, and the processing (e.g., filtering) comprises using the CGI measurement values to detect open circuits and out-of-compliance electrodes. For example, CGI measurement values above a first predetermined CGI threshold value (e.g., above 14 kΩ; above 30 kΩ; above 150 kΩ) can be indicative of electrodes having an abnormal interface with the tissue of the body portion and CGI measurement values below a second predetermined CGI threshold value (e.g., below 100Ω; below 500Ω; below 1 kΩ) can be indicative of electrodes being short circuited to ground.

In certain implementations, the processing (e.g., filtering) comprises generating a TI asymmetry dataset comprising TI asymmetry values based on the plurality of electrodes, and using the TI asymmetry values to detect out-of-compliance electrodes, calibration issues, and/or resolution issues. The TI asymmetry values between two distinct electrodes can be defined as the absolute difference of the TI measurement values when the roles of the stimulating electrode and the recording electrode are interchanged: Asymmetry=|TIM ($x=A$; $y=B$)–TIM($x=B$; $y=A$)|. For example, an electrode having more than a predetermined threshold number (e.g., more than 10; more than 11; more than 12; more than about half of the total number of electrodes) of TI asymmetry values that are above a predetermined TI asymmetry threshold value (e.g., above 5Ω; above 35Ω; above 100Ω) can be indicative of the electrode having an abnormal interface with the tissue of the body portion. In certain other implementations, other metrics can be used for asymmetry (e.g., by region or by row versus column).

In certain implementations, generating the TI gradient vector dataset in the operational block 420 comprises normalizing the TI measurement values in the operational block 520. The baseline transimpedance values for an electrode array can vary between devices (e.g., medical implants) and the normalization can be configured to reduce (e.g., minimize) the effect of such variations of the baseline TI values on the evaluation (e.g., estimation; determination; classification) of the pose (e.g., foldover status) of the elongate structure. The normalization of the TI measurement values can be performed prior to subsequent analysis or as part of the subsequent analysis, In certain implementations, the normalizing comprises determining a minimum TI value of the plurality of TI measurement values (e.g., a minimum TI value that have not been excluded by the processing of the TI measurement values in the operational block 510) and subtracting the minimum TI value from each of the TI measurement values (e.g., each of the TI measurement values that have not been excluded by the processing of the TI measurement values in the operational block 510). In certain other implementations, the normalizing comprises dividing each of the TI measurement values (e.g., that have not been excluded by the processing of the TI measurement values in the operational block 510) by the minimum TI value. In certain other implementations, the normalizing of the TI measurement values in the operational block 520 is excluded. For example, when looking at gradient phases, normalization can be excluded since phase angle is unaffected by magnitude. Similarly, noise threshold can be calculated as an offset above minimum measured value.

Figure 9:
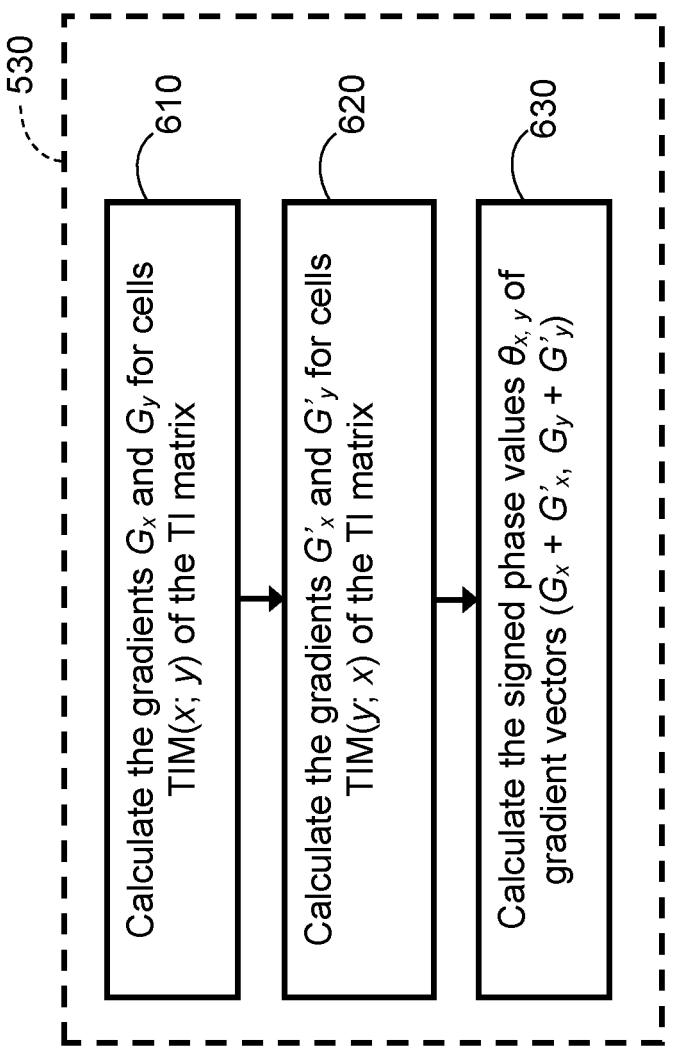
FIG. 9 is a flow diagram of an example method for calculating the plurality of TI gradient vector phase values in accordance with certain implementations described herein.

In certain implementations, generating the TI gradient vector dataset in the operational block 420 comprises calculating, in response at least in part to the TI measurement set, the plurality of TI gradient vector phase values in the operational block 530. FIG. 9 is a flow diagram of an example method 530 for calculating the plurality of TI gradient vector phase values in accordance with certain implementations described herein. In an operational block 610, calculating the plurality of TI gradient vector phase values in the operational block 530 comprises calculating the gradients $G_x$ and $G_y$ for cells TIM($x$; $y$) of the TI matrix in which the stimulating electrode x is basal relative to the recording electrode y with at least one electrode between the stimulating electrode and the recording electrode (e.g., cells TIM($x$; $y$) with $x < y-1$), with $G_x$ and $G_y$ defined as:

$$G_x = TIM(x+1;y) - TIM(x;y) \text{ and}$$

$$G_y = TIM(x;y-1) - TIM(x;y).$$

If none of the cells TIM($x+1$; $y$), TIM($x$; $y$), or TIM($x$; $y-1$) have been excluded by the processing of the TI measurement values in the operational block 510, then the gradients $G_x$ and $G_y$ for cell TIM($x$; $y$) are calculated. If any of the cells TIM($x+1$; $y$), TIM($x$; $y$), or TIM($x$; $y-1$) have been excluded by the processing of the TI measurement values in the operational block 510, then the gradients $G_x$ and $G_y$ for cell TIM($x$; $y$) are not calculated In an operational block 620, calculating the plurality of TI gradient vector phase values in the operational block 530 further comprises calculating the gradients $G'_x$ and $G'_y$ for cells TIM(y; x) of the TI matrix in which the roles of the recording electrode and the stimulating electrode are reversed (e.g., the electrode x is the recording electrode and the electrode y is the stimulating electrode), with $G'_x$ and $G'_y$ defined as:

$$G'_x = \text{TIM}(y;x+1) - \text{TIM}(y;x) \text{ and}$$

$$G'_y = \text{TIM}(y-1;x) - \text{TIM}(y;x).$$

If none of the cells TIM(y; x+1), TIM(y; x), or TIM(y−1; x) have been excluded by the processing of the TI measurement values in the operational block 510, then the gradients $G'_x$ and $G'_y$ for cell TIM(y; x) are calculated. If any of the cells TIM(y; x+1), TIM(y; x), or TIM(y−1; x) have been excluded by the processing of the TI measurement values in the operational block 510, then the gradients $G'_x$ and $G'_y$ for cell TIM(y; x) are not calculated.

In an operational block 630, calculating the plurality of TI gradient vector phase values in the operational block 530 further comprises calculating the signed phase values $\theta_{x,y}$ of gradient vectors $(G_x + G'_x, G_y + G'_y)$ (e.g., in degrees). For example, the signed phase values $\theta_{x,y}$ can be calculated using:

$$\theta_{x,y} =$$

$$\text{sign}\left((G_x + G'_x) - (G_y + G'_y)\right) \cdot \cos^{-1}\left(\frac{G_x + G'_x + G_y + G'_y}{\sqrt{2 \cdot \left((G_x + G'_x)^2 + (G_y + G'_y)^2\right)}}\right),$$

where $$\text{sign}(x) = \frac{x}{|x|}$$

when x≠0 and sign(0)=0. For other examples, the signed phase values $\theta_{x,y}$ can be calculated using the arctan 2 function or numerical methods (e.g., quadratic methods). In certain implementations, instead of calculating the signed phase values, the quadrant values can be calculated. In certain implementations, calculating the plurality of TI gradient vector phase values in the operational block 530 further comprises normalizing the calculated TI gradient vector phase values by subtracting a value (e.g., an average value or first principle components of the TI matrix from a population of non-folded insertions) and analyzing the residuals. In certain other implementations, the concentration of gradient phases can be observes with respect to the mean vector, a non-unimodal distribution of gradient phases can be identified, median absolute deviations can be utilized to identify outlier gradient phases, and can be tested for correlation with potential fold/buckle apex positions. In certain implementations, a logistic predictor can be used to predict the probability that a gradient (e.g., amplitude and phase) is an outlier and likely caused by a fold.

In certain implementations, generating the TI gradient vector dataset in the operational block 420 further comprises processing (e.g., filtering) the TI gradient vector phase values. For example, processing (e.g., filtering) the TI gradient vector phase values can comprise removing one or more TI gradient vector phase values from the TI gradient vector dataset, the removed one or more TI gradient vector phase values based at least in part on at least one electrode having either an abnormal interface with tissue of the body portion or a short circuit to ground. For example, TI gradient vector phase values can be excluded from further analysis if one or more of the following conditions (e.g., based on CGI measurement values and/or TI asymmetry values as described herein) are true:

the stimulating electrode has an abnormal electrode-tissue interface, the recording electrode has an abnormal electrode-tissue interface, the stimulating electrode and the recording electrode straddle an electrode that is short circuited to ground, or the stimulating electrode and/or the recording electrode is between two electrodes short circuited to ground.

In certain implementations, generating the TI gradient vector dataset in the operational block 420 comprises calculating (e.g., counting) a number of valid gradient vectors $(G_x + G'_x, G_y + G'_y)$ in the operational block 540. For example, if none of the cells TIM(x+1; y), TIM(x; y), TIM(x; y−1), TIM(y; x+1), TIM(y; x), or TIM(y−1; x) have been excluded by the processing of the TI measurement values in the operational block 510, then the gradient vector $(G_x + G'_x, G_y + G'_y)$ is counted as a valid TI gradient vector. If any of the cells TIM(x+1; y), TIM(x; y), TIM(x; y−1), TIM(y; x+1), TIM(y; x), or TIM(y−1; x) have been excluded by the processing of the TI measurement values in the operational block 510, then the gradient vector $(G_x + G'_x, G_y + G'_y)$ is not counted as a valid TI gradient vector.

In certain implementations, generating an evaluation of the pose of the elongate structure relative to the body portion in the operational block 430 comprises calculating, in response to the TI gradient vector dataset, a gradient phase range (GPR) value in the operational block 550. For example, the calculated GPR value can be equal to a difference between a maximum value $\theta_{max}$ of a selected subset of the TI gradient vector phase values $\theta_{x,y}$ and a minimum value $\theta_{min}$ of the selected subset of the TI gradient vector phase values $\theta_{x,y}$.

Figure 10:
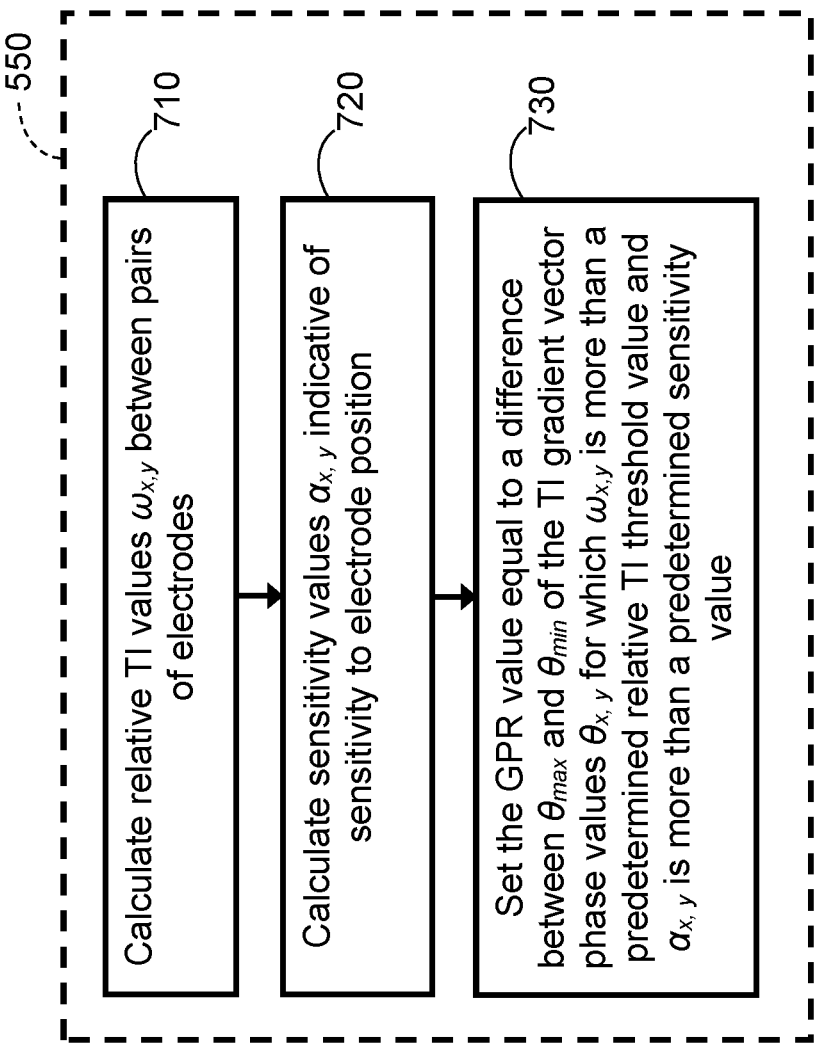
FIG. 10 is a flow diagram of an example method for calculating the GPR value in accordance with certain implementations described herein.

FIG. 10 is a flow diagram of an example method 550 for calculating the GPR value in accordance with certain implementations described herein. In an operational block 710, calculating the GPR value in the operational block 550 comprises calculating relative TI values $\omega_{x,y}$ between pairs of electrodes 148. For example, the relative TI value $\omega_{x,y}$ can equal the minimum value of a pair of TI measurement values of the cells TIM(x; y) and TIM(y; x):

$$\omega_{x,y} = \min[\text{TIM}(x;y), \text{TIM}(y;x)].$$

For other examples, the relative TI value $\omega_{x,y}$ can equal: the maximum value of the pair of TI measurement values of the cells TIM(x; y) and TIM(y; x), the mean value of the pair of TI measurement values of the cells TIM(x; y) and TIM(y; x), or the root-mean-squared (RMS) value of the pair of TI measurement values of the cells TIM(x; y) and TIM(y; x).

In an operational block 720, calculating the GPR value in the operational block 550 further comprises calculating sensitivity values $\alpha_{x,y}$ (e.g., indicative of sensitivity to electrode position). For example, the sensitivity value $\alpha_{x,y}$ can equal the minimum value of the length of the vectors $(G_x, G_y)$ and $(G'_x, G'_y)$:

$$\alpha_{x,y} = \min\left(\sqrt{G_x^2 + G_y^2}, \sqrt{G'^2_x + G'^2_y}\right).$$

For other examples, the sensitivity value $\alpha_{x,\,y}$ equals: the maximum value of the length of the vectors $(G_x, G_y)$ and $(G'_x, G'_y)$, the mean value of the length of the vectors $(G_x, G_y)$ and $(G'_x, G'_y)$, or the root-mean-squared (RMS) value of the length of the vectors $(G_x, G_y)$ and $(G'_x, G'_y)$.

In an operational block 730, calculating the GPR value in the operational block 550 further comprises setting the GPR value can be equal to a difference between the maximum value $\theta_{max}$ and the minimum value $\theta_{min}$ of the TI gradient vector phase values $\theta_{x,\,y}$ for which the relative TI value $\omega_{x,y}$ is more than a predetermined relative TI threshold value (e.g., more than $1\Omega$; more than $25\Omega$; more than $100\Omega$) and the sensitivity value $\alpha_{x,\,y}$ is more than a predetermined sensitivity value (e.g., more than $1\Omega$; more than $25\Omega$; more than $100\Omega$).

In certain implementations, generating an evaluation of the pose of the elongate structure relative to the body portion in the operational block 430 further comprises setting the evaluation in the operational block 560. In certain implementations, the evaluation can be set based on the calculated GPR value (e.g., as calculated in the operational block 550) and the number of valid TI gradient vectors (e.g., as calculated in the operational block 540). For example, the evaluation can be set to:

a folded pose evaluation if the calculated GPR value is greater than a predetermined GPR threshold value (e.g., greater than 105);

an unfolded pose evaluation if the calculated GPR value is less than or equal to the predetermined GPR threshold value and the number of valid TI gradient vectors is greater than or equal to a predetermined threshold number (e.g., greater than or equal to 153); and an inconclusive pose evaluation if the calculated GPR value is less than or equal to the predetermined GPR threshold value and the number of valid TI gradient vectors is less than the predetermined threshold number.

In certain implementations, generating an evaluation of the pose of the elongate structure relative to the body portion in the operational block 430 further comprises, upon the evaluation being set to a folded pose evaluation, determining an estimated foldover apex A of the elongate structure. For example, for each cell TIM(x; y) of the TI matrix in which the stimulating electrode is basal relative to the recording electrode with at least one electrode between the stimulating electrode and the recording electrode (e.g., each cell TIM(x; y) with x<y−1), the relative TI values $\omega_{x,y}$ and the signed phase values $\theta_{x,\,y}$ can be used to calculate a ridge score $q_{x,\,y}$ for the cell TIM(x; y) with $q_{x,\,y}$ equal to the product of the relative TI value and the absolute value of the signed phase value: $q_{x,y}=\omega_{x,y}\cdot|\theta_{x,y}|$. The ridge scores $q_{x,\,y}$ can be grouped according to the potential fold apex $a=(x+y)/2$, and the root-mean-squared (RMS) value of the ridge scores $q_{x,\,y}$ can be computed for each group:

$$Q_a = \frac{1}{N} \cdot \sqrt{\sum_{(x,y)} q_{x,y}^2}$$

where N is the number of ridge scores in the group. The estimated foldover apex A can be selected to be the value of potential fold apex a which has the highest $Q_a$ value. In certain implementations, an offset (e.g., one-half of an electrode spacing) can be added to the fold apex location to improve overall accuracy.

In another example, the estimated foldover apex A can be calculated using linear regression of potential foldover locations $(q_a)$, then calculating a point of intersection with the main diagonal of the TI matrix (e.g., cells TIM(x=y)). Certain other implementations described herein utilize other methods of determining the estimated foldover apex A. For example, instead of using the RMS value of the ridge scores $q_{x,\,y}$, the mean value of the ridge scores $q_{x,\,y}$ can be used. For another example, in certain implementations, a linear regression of potential fold-over locations is calculated, and the point of intersection with the main diagonal of the TI matrix is determined. Other ridge detection techniques (e.g., edge detection) can be used to detect the point of intersection with the main diagonal of the TI matrix.

In certain implementations, instead of using the calculated GPR value for evaluating (e.g., estimating; determining; classifying) the foldover status of the elongate structure, a mean gradient phase angle can be analyzed across multiple cells of the TI matrix and can be compared to one or more expected extreme values distinguishing a folded state from an unfolded state. In certain implementations, statistics regarding the gradient phase values of the TI matrix can be calculated and can be compared to one or more expected extreme values distinguishing a folded state from an unfolded state (e.g., a Rayleigh test). In certain implementations, the gradient phase values and/or normalized gradient phase values can be checked for a bimodal distribution. In certain implementations, a circular dispersion can be calculated for the gradient phase values and can be compared to a predetermined threshold. In certain implementations, in evaluating the gradient phase values, the gradient phase values can be weighted by the gradient magnitude values such that gradient phase values for longer gradient vectors are weighed more highly than are gradient phase values for shorter gradient vectors. In certain implementations, the gradients can be examined at multiple scales and/or resolutions (e.g., across more than merely adjacent cells of the TI matrix).

In certain implementations, communicating at least one evaluation (e.g., status of the pose; changes of the pose), in real-time (e.g., during the implantation and/or retraction) in the operational block 440 comprises communicating the at least one evaluation to either a user (e.g., medical professional; surgeon; operator of an insertion system being used for the implantation) or an automated surgical system performing the implantation. The at least one evaluation of the pose can be generated using measurement values generated during implantation and/or retraction of the structure into and/or from the body portion and can be used to facilitate implantation and/or retraction of the structure. For example, the at least one controller 330 can be configured to generate at least one status reporting signal comprising the information 342 to be communicated via the at least one output interface 340 (e.g., wired and/or wireless ports). The at least one status reporting signal can be received by at least one communication device (e.g., display device; screen; status indicator light; audio device; speaker; vibration motor) configured to communicate the at least one evaluation of the pose of the elongate structure to the user or by an automated insertion system (e.g., an actuator of an automated or robotic insertion system). The user and/or automated insertion system can then respond real-time to the at least one status reporting signal by manipulating the structure (e.g., by proceeding with the implantation/retraction; to take corrective actions to avoid sub-optimal poses).

Although commonly used terms are used to describe the systems and methods of certain implementations for ease of understanding, these terms are used herein to have their broadest reasonable interpretations. Although various aspects of the disclosure are described with regard to illustrative examples and implementations, the disclosed examples and implementations should not be construed as limiting. Conditional language, such as, among others, "can," "could," "might," or "may," unless specifically stated otherwise, or otherwise understood within the context as used, is generally intended to convey that certain implementations include, while other implementations do not include, certain features, elements and/or steps. Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

It is to be appreciated that the implementations disclosed herein are not mutually exclusive and may be combined with one another in various arrangements. In addition, although the disclosed methods and apparatuses have largely been described in the context of conventional cochlear implants, various implementations described herein can be incorporated in a variety of other suitable devices, methods, and contexts. More generally, as can be appreciated, certain implementations described herein can be used in a variety of implantable medical device contexts that can benefit from having at least a portion of the received power available for use by the implanted device during time periods in which the at least one power storage device of the implanted device unable to provide electrical power for operation of the implantable medical device.

Language of degree, as used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within ±10% of, within ±5% of, within ±2% of, within ±1% of, or within ±0.1% of the stated amount. As another example, the terms "generally parallel" and "substantially parallel" refer to a value, amount, or characteristic that departs from exactly parallel by ±10 degrees, by ±5 degrees, by ±2 degrees, by ±1 degree, or by ±0.1 degree, and the terms "generally perpendicular" and "substantially perpendicular" refer to a value, amount, or characteristic that departs from exactly perpendicular by ±10 degrees, by ±5 degrees, by ±2 degrees, by ±1 degree, or by ±0.1 degree. The ranges disclosed herein also encompass any and all overlap, sub-ranges, and combinations thereof. Language such as "up to," "at least," "greater than," "less than," "between," and the like includes the number recited. As used herein, the meaning of "a," "an," and "said" includes plural reference unless the context clearly dictates otherwise. Also, as used in the description herein, the meaning of "in" includes "into" and "on," unless the context clearly dictates otherwise.

While the methods and systems are discussed herein in terms of elements labeled by ordinal adjectives (e.g., first, second, etc.), the ordinal adjective are used merely as labels to distinguish one element from another (e.g., one signal from another or one circuit from one another), and the ordinal adjective is not used to denote an order of these elements or of their use.

The invention described and claimed herein is not to be limited in scope by the specific example implementations herein disclosed, since these implementations are intended as illustrations, and not limitations, of several aspects of the invention. Any equivalent implementations are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example implementations disclosed herein, but should be defined only in accordance with the claims and their equivalents.

What is claimed is:

1. A system comprising:
at least one data input interface configured to receive data from a plurality of transducers of a medical device configured to be implanted on or in a recipient;
at least one controller in operative communication with the at least one data input interface, the at least one controller configured to:
receive a plurality of measurement values generated using the plurality of transducers of the medical device in and/or on a body portion of a recipient during implantation of the medical device;
utilize the plurality of measurement values to generate a plurality of gradient vector phase values; and
generate, in response at least in part to the plurality of gradient vector phase values, intra-operative feedback information indicative of sub-optimal conditions of a pose of the medical device during the implantation of the medical device, the sub-optimal conditions to be corrected during the implantation and in response to the intra-operative feedback information;
at least one output interface in operative communication with the at least one controller, the at least one output interface configured to provide the intra-operative feedback information during the implantation of the medical device; and
an actuator configured to manipulate the medical device in response to the intra-operative feedback information.

2. The system of claim 1, further comprising at least one control output interface in operative communication with the at least one controller, the at least one control output interface configured to transmit control signals to the plurality of transducers, the plurality of transducers responsive to the control signals by generating the data.

3. The system of claim 1, wherein the at least one controller comprises at least one processor and at least one storage device in operative communication with the at least one processor.

4. The system of claim 3, wherein the at least one storage device is configured to collect and store the data.

5. The system of claim 1, wherein the medical device comprises a stimulation assembly of a cochlear implant auditory prosthesis, and the body portion comprises a cochlea of the recipient.

6. The system of claim 1, wherein the at least one controller is configured to transmit the control signals to the plurality of transducers automatically during the implantation of the medical device.

7. The system of claim 1, further comprising at least one user input interface in operative communication with the at least one controller, the at least one controller configured to receive triggering signals from the at least one user input interface intermittently during the implantation of the medical device, wherein the at least one controller is configured to respond to the triggering signals by transmitting the control signals to the plurality of transducers.

8. The system of claim 1, wherein the at least one output interface is configured to be in operative communication with at least one status communication device configured to respond to the intra-operative feedback information by communicating a status signal indicative of the pose of the medical device.

9. The system of claim 7, wherein the at least one user input interface and the at least one output interface are configured to be in operative communication with a computing device configured to be utilized by a medical professional.

10. The system of claim 1, wherein the actuator is part of an automated insertion system, and the at least one output interface is configured to be in operative communication with the automated insertion system, the automated insertion system configured to respond automatically and in real-time to the intra-operative feedback information by using the actuator to manipulate the medical device to correct the sub-optimal conditions in real-time during the implantation.

11. A method comprising:

receiving a measurement set comprising a plurality of measurement values generated using a plurality of electrodes distributed along an elongate structure configured to be implanted in and/or on a body portion of a recipient, the measurement set indicative of a pose of the elongate structure relative to the body portion;

generating, in response at least in part to the measurement set and using a processor, a gradient vector dataset comprising a plurality of gradient vector phase values;

generating, in response at least in part to the plurality of gradient vector phase values of the gradient vector dataset and using the processor, intra-operative feedback information indicative of non-optimal conditions of the pose of the elongate structure relative to the body portion during implantation of the elongate structure, the non-optimal conditions to be corrected during the implantation and in response to the intra-operative feedback information by an operator performing the implantation;

communicating, using an interface in operable communication with the processor, the intra-operative feedback information to the operator during the implantation; and responding to the intra-operative feedback information by manipulating the elongate structure to correct the sub-optimal conditions of the pose.

12. The method of claim 11, wherein the plurality of measurement values comprises a plurality of transimpedance measurement values and the plurality of gradient vector phase values comprises a plurality of transimpedance gradient vector phase values.

13. The method of claim 11, wherein the plurality of measurement values comprises a plurality of voltage measurement values and the plurality of gradient vector phase values comprises a plurality of voltage gradient vector phase values.

14. The method of claim 11, wherein the operator is a medical professional using an insertion system to implant the elongate structure into the body portion or an automated surgical system performing the implantation.

15. The method of claim 11, wherein generating the gradient vector dataset comprises removing one or more measurement values from the measurement set, the removed one or more measurement values generated using at least one electrode having either an abnormal interface with tissue of the body portion or a short circuit to ground.

16. The method of claim 11, wherein generating the gradient vector dataset comprises removing one or more gradient vector phase values from the gradient vector dataset, the removed one or more gradient vector phase values based on at least one electrode having either an abnormal interface with tissue of the body portion or a short circuit to ground.

17. The method of claim 15, further comprising receiving a common ground impedance (CGI) measurement set comprising CGI measurement values generated using the plurality of electrodes, wherein CGI measurement values above a first predetermined CGI threshold value are indicative of electrodes having an abnormal interface with the tissue of the body portion and CGI measurement values below a second predetermined CGI threshold value are indicative of electrodes short circuited to ground.

18. The method of claim 15, further comprising generating an asymmetry dataset comprising asymmetry values based on the plurality of electrodes, wherein an electrode having more than a predetermined threshold number of asymmetry values that are above a predetermined asymmetry threshold value is indicative of the electrode having an abnormal interface with the tissue of the body portion.

19. The method of claim 11, further comprising normalizing the measurement values prior to said generating gradient vector dataset.

20. The method of claim 11, wherein the plurality of measurement values comprises a transimpedance matrix of a plurality of cells TIM(x; y) and generating the gradient vector dataset comprises:

calculating gradients $G_x$ and $G_y$ for cells TIM(x; y) in which an electrode x is a stimulating electrode and an electrode y is a recording electrode, the stimulating electrode basal relative to the recording electrode with at least one electrode between the stimulating electrode and the recording electrode, with $G_x$ and $G_y$ defined as: $G_x$=TIM(x+1; y)–TIM(x; y) and $G_y$=TIM(x; y–1)–TIM(x; y); and calculating gradients $G'_x$ and $G'_y$ for cells TIM(y; x) in which the electrode x is the recording electrode and the electrode y is the stimulating electrode, with $G'_x$ and $G'_y$ defined as: $G'_x$=TIM(y; x+1)–TIM(y; x) and $G'_y$=TIM(y–1; x)–TIM(y; x); and calculating the phase values $\theta_{x,\ y}$ of gradient vectors $(G_x+G'_x,\ G_y+G'_y)$.

21. The method of claim 20, wherein generating the evaluation of the pose comprises calculating a gradient phase range (GPR) value, said calculating the GPR value comprising:

calculating relative TI values $\omega_{x,y}$ between pairs of electrodes, the relative TI value $\omega_{x,y}$ equal to a minimum value of a pair of TI measurement values of the cells TIM(x; y) and TIM(y; x);

calculating sensitivity values $\alpha_{x,\ y}$ indicative of sensitivity to electrode position, the sensitivity value $\alpha_{x,\ y}$ equal to a minimum value of the length of the vectors $(G_x, G_y)$ and $(G'_x, G'_y)$; and setting the GPR value equal to a difference between a maximum value $\theta_{max}$ and a minimum value $\theta_{min}$ of the TI gradient vector phase values $\theta_{x,\ y}$, for which the relative TI value $\omega_{x,y}$ is more than a predetermined relative TI threshold value and the sensitivity value $\alpha_{x,\ y}$ is more than a predetermined sensitivity value.

22. The method of claim 11, wherein generating the gradient vector dataset comprises calculating, in response to the gradient vector dataset, a number of valid gradient vectors of the gradient vector dataset, and said generating an evaluation comprises:

calculating, in response to the gradient vector dataset, a gradient phase range value, the gradient phase range (GPR) value equal to a difference between a maximum value of the gradient vector phase values and a minimum value of the gradient vector phase values; and setting the evaluation to:

a folded pose evaluation if the calculated GPR value is greater than a predetermined GPR threshold value;

an unfolded pose evaluation if the GPR value is less than or equal to the predetermined GPR threshold value and the number of valid gradient vectors is greater than or equal to a predetermined threshold number; and an inconclusive pose evaluation if the GPR value is less than or equal to the predetermined GPR threshold value and the number of valid gradient vectors is less than the predetermined threshold number.

23. The method of claim 11, wherein setting the evaluation to a folded pose evaluation further comprises determining an estimated foldover apex of the elongate structure.

24. The method of claim 11, wherein the elongate structure comprises an electrode array of a cochlear implant, the electrode array configured to be inserted at least partially into a cochlea of the recipient.

25. The method of claim 11, wherein the measurement set is generated and received during the implantation of at least the portion of the elongate structure in and/or on a body portion of a recipient.

26. The system of claim 1, wherein the medical device comprises a stimulation assembly of a cochlear implant auditory prosthesis, at least a portion of the stimulation assembly configured to be implanted in a cochlea of the recipient, the plurality of transducers comprising electrodes of the stimulation assembly, and the sub-optimal conditions comprising a folded state or snagged state of the stimulation assembly.

27. The system of claim 1, wherein the intra-operative feedback information is indicative of existence and position of foldover of a portion of the medical device within the body portion.

28. The method of claim 11, wherein the operator comprises a robotic surgical system and the method further comprises controlling the robotic surgical system in response to the intra-operative feedback information to avoid the sub-optimal conditions of the pose.

29. A method comprising:

repeatedly, during implantation of an elongate structure into and/or on a body portion of a recipient, using a processor to:

receive a measurement set comprising a plurality of measurement values generated using a plurality of electrodes distributed along the elongate structure, the measurement set indicative of a pose of the elongate structure relative to the body portion;

generate a plurality of gradient vector phase values in response at least in part to the measurement set; and generate intra-operative feedback information in response at least in part to the plurality of gradient vector phase values, the intra-operative feedback information indicative of the pose of the elongate structure relative to the body portion; and when the intra-operative feedback information is indicative of non-optimal conditions of the pose of the elongate structure during the implantation, manipulating the elongate structure to avoid the non-optimal conditions.

30. The method of claim 29, wherein the plurality of measurement values comprises a plurality of transimpedance measurement values and the plurality of gradient vector phase values comprises a plurality of transimpedance gradient vector phase values.

31. The method of claim 29, wherein the plurality of measurement values comprises a plurality of voltage measurement values and the plurality of gradient vector phase values comprises a plurality of voltage gradient vector phase values.

32. The method of claim 29, wherein the measurement set comprises a common ground impedance (CGI) measurement set comprising CGI measurement values generated using the plurality of electrodes, wherein CGI measurement values above a first predetermined CGI threshold value are indicative of electrodes having an abnormal interface with the tissue of the body portion and CGI measurement values below a second predetermined CGI threshold value are indicative of electrodes short circuited to ground.

33. The method of claim 29, wherein the elongate structure comprises an electrode array of a cochlear implant, the electrode array configured to be inserted at least partially into a cochlea of the recipient.

* * * * *